(12) United States Patent
Jones et al.

(10) Patent No.: US 8,148,128 B2
(45) Date of Patent: Apr. 3, 2012

(54) CHEMICALLY MODIFIED MUTANT SERINE HYDROLASES SHOW IMPROVED CATALYTIC ACTIVITY AND CHIRAL SELECTIVITY

(75) Inventors: John Bryan Jones, Lakefield (CA); Michael Dickman, Winnipeg (CA); Richard C. Lloyd, Chesterton (GB)

(73) Assignee: The Governing Council of the University of Toronto, Toronto, Ontario (CA)

( * ) Notice: Subject to any disclaimer, the term of this patent is extended or adjusted under 35 U.S.C. 154(b) by 304 days.

(21) Appl. No.: 12/234,399

(22) Filed: Sep. 19, 2008

(65) Prior Publication Data
US 2009/0075329 A1 Mar. 19, 2009

Related U.S. Application Data

(63) Continuation of application No. 10/791,093, filed on Mar. 1, 2004, now abandoned, which is a continuation of application No. 09/436,513, filed on Nov. 9, 1999, now abandoned.

(60) Provisional application No. 60/107,758, filed on Nov. 10, 1998, provisional application No. 60/113,061, filed on Dec. 21, 1998.

(51) Int. Cl.
*C12N 9/52* (2006.01)
*C12N 9/54* (2006.01)
*C12N 15/57* (2006.01)
*C12N 15/75* (2006.01)

(52) U.S. Cl. .. 435/220; 435/69.1; 435/221; 435/252.31; 435/320.1; 536/23.2; 544/42

(58) Field of Classification Search .................. None
See application file for complete search history.

(56) References Cited

U.S. PATENT DOCUMENTS

| 5,116,741 A * | 5/1992 | Bryan et al. ................ 435/87 |
| 5,208,158 A | 5/1993 | Bech et al. |
| 5,244,791 A | 9/1993 | Estell |
| 5,316,935 A * | 5/1994 | Arnold et al. .............. 435/222 |

(Continued)

FOREIGN PATENT DOCUMENTS

EP 0 328 229 A1 8/1989

(Continued)

OTHER PUBLICATIONS

Berglund, P., et al., 1996, "Altering the specificity of subtilisin *B. lentus* by combining mutagenesis and chemical modification", Bioorganic & Medicinal Chemistry Letters, vol. 6, pp. 2507-2512.*

(Continued)

*Primary Examiner* — Manjunath Rao
*Assistant Examiner* — William W Moore
(74) *Attorney, Agent, or Firm* — Danisco US Inc.

(57) ABSTRACT

This invention provides novel chemically modified mutant serine hydrolases that catalyze a transamidation and/or a transpeptidation and/or a transesterification reaction. The modified serine hydrolases have one or more amino acid residues in a subsite replaced with a cysteine, wherein the cysteine is modified by replacing the thiol hydrogen in the cysteine with a substituent group providing a thiol side chain comprising a moiety selected from the group consisting of a polar aromatic substituent, an alkyl amino group with a positive charge, and a glycoside. In particularly preferred embodiments, the substitutents include an oxazolidinone, a $C_1$ to $C_{15}$ alkyl amino group with a positive charge, or a glycoside.

4 Claims, 5 Drawing Sheets

| 13 R = H | 17 R = H, n = 3 | 1c R = H, n = 3 |
| (R)-14 R = iPr | (R)-18 R = iPr, n = 3 | (R)-1d R = iPr, n = 3 |
| (R)-15 R = Ph | (R)-19 R = Ph, n = 3 | (R)-1e R = Ph, n = 3 |
| (R)-16 R = Bn | (R)-20 R = Bn, n = 3 | (R)-1f R = Bn, n = 3 |
| | (R)-21 R = Ph, n = 2 | (R)-1g R = Ph, n = 2 |
| | (R)-22 R = Bn, n = 2 | (R)-1h R = Bn, n = 2 |

Reagents: (i) KOH, DMSO, Br$(CH_2)_n$Br; (ii) NaSSO$_2$CH$_3$, DMF.

U.S. PATENT DOCUMENTS

| | | | |
|---|---|---|---|
| 5,316,941 A | 5/1994 | Estell et al. | |
| 5,403,737 A | 4/1995 | Abrahmsen et al. | |
| 5,629,173 A * | 5/1997 | Abrahmsen et al. | 435/68.1 |
| 5,955,340 A | 9/1999 | Bott | |
| 6,277,617 B1 * | 8/2001 | Bott et al. | 435/219 |
| 6,284,512 B1 * | 9/2001 | Jones et al. | 435/221 |
| 6,379,942 B1 * | 4/2002 | Davis et al. | 435/221 |
| 6,395,532 B1 * | 5/2002 | Jones | 435/222 |
| 6,512,098 B2 * | 1/2003 | Jones et al. | 530/408 |
| 6,576,454 B2 * | 6/2003 | Jones | 435/222 |
| 6,930,180 B2 * | 8/2005 | Jones et al. | 536/4.1 |
| 7,371,553 B2 * | 5/2008 | Davis et al. | 435/219 |

FOREIGN PATENT DOCUMENTS

| | | | |
|---|---|---|---|
| WO | WO 91/16423 | | 4/1991 |
| WO | WO 96/27671 | | 2/1996 |
| WO | WO 97/37007 | | 10/1997 |
| WO | WO 98/23732 | * | 6/1998 |
| WO | WO 99/20723 | | 4/1999 |
| WO | WO 99/37323 | | 7/1999 |
| WO | WO 99/37324 | | 7/1999 |
| WO | WO 00/01712 | | 1/2000 |
| WO | WO 00/28007 | | 5/2000 |
| WO | WO 00/37658 | | 6/2000 |

OTHER PUBLICATIONS

Bergland, P., et al., 1997, "Chemical modification of cysteine mutants of subtilisin *Bacillus lentus* can create better catalysts than the wild-type enzyme", Journal of the American Chemical Society, vol. 119, No. 22, pp. 5265-5266.*

Davis, B., et al., 1998, "Controlled site-selective glycosylation of proteins by a combined site-directed mutagenesis and chemical modification approach", Journal of Organic Chemistry, vol. 63, No. 26, pp. 9614-19615.*

DeSantis, G, et al., 1998, "Site-directed mutagenesis combined with chemical modification as a strategy for altering the specificity of the S1 and S1' pockets of subtilisin *Bacillus lentus*", Biochemistry, vol. 37, No. 17, pp. 5968-5973.*

Dickman, M., et al., 1998, "Chemically modified mutants of *Bacillus lentus* subtilisin catalyze transesterification reactions better than wild type", Tetrahedron: Asymmetry, vol. 9, No. 23, pp. 4099-4102.*

*Abrahmsen et al., "Engineering Subtilisin and Its Subtrates for Efficient Ligation of Peptide Bonds in Aqueous Solution," *Biochemistry*, 30:4151-59 (1991).

*Akabas et al., "Acetylcholine Receptor Channel Structure Probed in Cysteine-Substitution Mutants," *Science*, 258:307-310 (1992).

*Alvear et al., "Inactivation of Chicken Liver Mevalonate 5-Diphosphate Decarboxylase by Sulfhydryl-Directed Reagents: Evidence of a Functional Dithiol," *Biochimica et Biophysica Acta*, 994:7-11 (1989).

*Barbas et al., "A Search for Peptide Ligase: Cosolvent-Mediated Conversion of Proteases to Esterases for Irreversible Synthesis of Peptides," *J. Am. Chem. Soc.*, 110:5162-66 (1988).

*Barbas, et al., "Papain Catalysed Peptide Synthesis: Control of Amidase Activity and the Introduction of Unusual Amino Acids," *J. Chem. Soc., Chem. Commun.*, 533-34 (1987).

*Bech et al., "Significance of Hydrophobic $S_4$-$P_4$ Interactions in Subtilisin 309 from *Bacillus lentus*," *Biochemistry*, 32:2847-2852 (1993).

*Bech, LM et al "Cemical Modifications of a Cysteinyl Residue Introduced in the Binding Site of Carboxypeptidase Y by Site-Directed Mutagenesis," *Carlsberg Research Communications*, (1988) vol. 53, pp. 381-393.

*Bell et al., "Kinetic Studies on the Peroxidase Activity of Selenosubtilisin," *Biochemistry*, 32:3754-3762 (1993).

*Betzel et al., "Crystal Structure of the Alkaline Proteinase Savinase™ from *Bacillus lentus* at 1.4 Å Resolution," *J. Mol. Biol.*, 223:427-445(1992).

*Bodwell et al., "Sulfhydryl-Modifying Reagents Reversibly Inhibit Binding of Glucocorticoid-Receptor Complexes to DNA-Cellulos," *Biochemistry*, 23:1392-1398 (1984).

*Bonneau et al., "Alteration of the Specificity of Subtilisin BPN' by Site-Directed Mutagenesis in its $S_1$ and $S_1$ ' Binding Sites," *J. Am. Chem. Soc.*, 113:1026-30 (1991).

*Brocklehurst, "Specific Covalent Modification of Thiols: Applications in the Study of Enzymes and Other Biomolecules," *Int. J. Biochem.*, 10:259-274 (1979).

*Bruice et al., "Novel Alkyl Alkanethiolsulfonate Sulfhydryl Reagents. Modification of Derivatives of L-Cysteine," *Journal of Protein Chemistry*, 1:47-58 (1982).

*Buckwalter et al., "Improvement in the Solution Stability of Porcine Somatotropin by Chemical Modification of Cysteine Residues," *J. Agric. Food Chem.*, 40:356-362 (1992).

*Chen et al., "Incorporation of Unnatural Amino Acid Derivatives into a Peptide Bond via an Oxime Ester Catalysed By Papain or Lipase," *Chem. Commun.*, 165-66 (1996).

*Chen et al., "Kinetically Controlled Peptide Bond Formation in Anhydrous Alcohol Catalyzed by the Industrial Protease Alcalase," *J. Org. Chem.*, 57:6960-65 (1992).

*Chen et al., "Probing the S-1' Subsite Selectivity of an Industrial Alkaline Protease in Anhydrous t-Butanol," *Bioorganic & Medicinal Chemistry Letters*, 3(4):727-33 (1993).

*Daly et al., "Formation of Mixed Disulfide Adducts at Cysteine-281 of the Lactose Repressor Protein Affects Operator and Inducer Binding Parameters," *Biochemistry*, 25:5468-5474 (1986).

*Davies et al., "A Semisynthetic Metalloenzyme Based on a Protein Cavity That Catalyzes the Enantiosleective Hydrolysis of Ester and Amide Substrates," *J. Am. Chem. Soc.*, 119:11643-11652 (1997).

*Davis, B.G., et al., "Altering the specificity of subtilisin *Bacillus lentus* through the introduction of positive charge at single amino acid sites," *Bioorganic and Medicinal Chemistry*, (Nov. 1999) 7 (11) 2303-11, XPO000892841.

*Davis, B.G., et al., "Controlled site selective protein glycosylation for precise glycan structure catalytic activity relationships," Biorganic & Medicinal Chemistry, vol. 8, 2000, pp. 1527-1535.

*Davis, B.G., et al., "Glycomethanethiosulfonates: powerful reagents for protein glycosylation," Tetrahedron: Asymmetry, NL, Elsevier Science Publishers, Amsterdam, vol. 11, No. 1, Jan. 2000, pp. 245-262.

*Davis, B.G., et al., "Glycosyldisulfides: a new class of solution and solid phase glycosyl donors," Chem. Commun, 2001, pp. 189-190.

*Davis, B.G., et al., "The controlled introduction of multiple negative charge at single amino acid sites in subtilisin *Bacillus lentus*," *Bioorganic and Medicinal Chemistry*, (Nov. 1999) 7 (11) 2293-301, XPO000892840.

*Davis, Benjamin G, et al., "The Controlled Glycosylation of a Protein with a Bivalent Glycan: Towards a New Class of Glycoconjugates, Glycodendriproteins," *Chem. Commun*, 2001, pp. 351-352.

*DeSantis et al., "Chemical Modifications at a Single Site Can Induce Significant Shifts in the pH Profiles of a Serine Protease," *J. Am Chem. Soc.*, 120:8582-8586 (1998).

*Desantis, G., et al, "Probing the altered specificity and catalytic properties of mutant subtilisin chemically modified at position S156C and S166C in the S1 pocket," Bioorganic and Medicinal Chemistry, (1997) 7/7 (1381-1387), XP0000892843.

*Di Bello, "Total Synthesis of Proteins by Chemical Methods: The Horse Heart Cytochrome C Example," *Gazzetta Chimica Italiana*, 126:189-197 (1996).

*Dime, DS., "Protein Topology and Ion Channel Research," Toronto Research Chemicals, Inc. (catalog date unknown).

*Ekberg et al., "Enzymatic Coupling of Two D-Amino Acid Residues in Aqueous Media," *Tetrahedron Letters*, 30(5):583-86 (1989).

*Engler et al., "Critical Functional Requirement for the Guanidinium Group of the Arginine 41 Side Chain of Human Epidermal Growth Factor as Revealed by Mutagenic Inactivation and Chemical Reactivation," *The Journal of Biological Chemistry*, 267:2274-2281 (1992).

*Frillingos et al., "Cysteine-Scanning Mutagenesis of Helix II and Flanking Hydrophilic Domains in the Lactose Permease of *Escherichia coli*," *Biochemistry*, 36:269-273 (1997).

*Gloss et al., "Examining the Structural and Chemical Flexibility of the Active Site Base, Lys-258, of *Escherichia coli* Aspartate Aminotransferase by Replacement with Unnatural Amino Acids," *Biochemistry*, 34:12323-12332 (1995).
*Graycar et al., "Altering the Proteolytic Activity of Subtilisin through Protein Engineering," *Annals New York Academy of Science*, 672:71-79 (1992).
*Gron et al., "A Highly Active and Oxidation-Resistant Subtilisin-Like Enzyme Produced by a Combination of Site-Directed Mutagenesis and Chemical Modification," *Eur. J. Biochem.*, 194:897-901 (1990).
*Gron et al., "Extensive Comparison of the Substrate Preferences of Two Subtilisins As Determined with Peptide Substrates Which Are Based on the Principle of Intramolecular Quenching," *Biochemistry*, 31(26):6011-18 (1992).
*Hempel et al., "Selective Chemical Modification of Human Liver Aldehyde Dehydrogenases $E_1$ and $E_2$ by Iodoacetamide," *The Journal of Biological Chemistry*, 256:10889-10896 (1981).
*Hilvert et al., "A Highly Active Thermophilic Semisynthetic Flavoenzyme," *J. Am. Chem. Soc.*, 110:682-689 (1988).
*Hilvert et al., "New Semisynthetic Flavoenzyme Based on a Tetrameric Portein Template, Glyceraldehyde-3-Phosphate Dehydrogenase," *J. Am. Chem. Soc.*, 107:5805-5806 (1985).
*House et al., "$^1$H NMR Spectroscopic Studies of Selenosubtilisin," *Biochemistry*, 32:3468-3473 (1993).
*Huang et al., "Improving the Activity of Immobilized Subtilisin by Site-Specific Attachment to Surfaces," *Anal. Chem.*, 69:4601-4607 (1997).
International Search Report, International Application No. PCT/US99/26586 dated Apr. 11, 2000, 6 pages.
*Jonsson et al., "Temperature Effects on Protease Catalyzed Acyl Transfer Reactions in Organic Media," *Journal of Molecular Catalysis B: Enzymatic*, 2:43-51 (1996).
*Kaiser, "Catalytic Activity of Enzymes Altered at Their Active Sites," *Agnew. Chem. Int. Ed. Engl.*, 27-913-922 (1988).
*Kanaya et al., "Role of Cysteine Residues in Ribonuclease H from *Escherichia coli*," *Biochem. J.*, 271:59-66 (1990).
*Kato et al., "First Stereoselective Synthesis of D-Amino Acid N-Alkyl Amide Catalyzed by D-Aminopeptidase," *Tetrahedron*, 45(18) 5743-54 (1989).
*Kawase et al., "Effect of Chemical Modification of Tyrosine Residues on Activities of Bacterial Lipase," *Journal of Fermentation and Bioengineering*, 72:317-319 (1991).
*Kawashiro et al., "Effect of Ester Moiety of Substrates on Enantioselectivity of Protease Catalysis in Organic Media," *Biochemistry Letters*, 18(12):1381-86 (1996).
*Kenyon et al., "Novel Sulfhydryl Reagents," *Methods Enzymol.*, 47:407-430 (1977).
*Kirley, "Reduction and Fluorescent Labeling of Cyst(e)ine-Containing Proteins for Subsequent Structural Analyses," *Analytical Biochemistry*, 180:231-236 (1989).
*Kluger et al., "Amino Group Reactions of the Sulfhydryl Reagent Methyl Methanesulfonothioate. Inactivation of D-3-hydroxybutyrate Dehydrogenase and Reaction with Amines in Water," *Can. J. Biochem.*, 58:629-632 (1980).
*Kokubo et al., "Flavohemoglobin: A Semisynthetic Hydroxylase Acting in the Absence of Reductase," *J. Am. Chem. Soc.*, 109:606-607 (1987).
*Konigsberg, "Reduction of Disulfide Bonds in Proteins with Dithiothreitol," *Methods in Enzymology*, 25:185-188 (1972).
*Kuang et al., "Enantioselective Reductive Amination of α-Amino Acids by a Pyridoxamine Cofactor in A Protein Cavity," *J. Am. Chem. Soc.*, 118:10702-10706 (1996).
*Lewis et al., "Determination of Interactive Thiol Ionizations in Bovine Serum Albumin, Glutathione, and Other Thiols by Potentiometric Difference Titration," *Biochemistry*, 19:6129-6137 (1980).
*Liu et al., "Site-Directed Fluorescence Labeling of P-Glycoprotein on Cysteine Residues in the Nucleotide Binding Domains," *Biochemistry*, 35:11865-11873 (1996).
*Lloyd, R.C. et al., "Site Selective Glycosilation of Subtilisin *Bacillus lentus* Causes Dramatic Increase in Esterase Activity," *Biorganic & Medicinal Chemistry*, vol. 8, 2000, pp. 1537-1544.

*Margolin et al., "Incorporation of D-Amino Acids into Peptides via-Enzymatic Condensation in Organic Solvents," *J. Am. Chem. Soc.*, 109:7885-87 (1987).
*Margolin et al., "Peptide Synthesis Catalyzed by Lipases in Anhydrous Organic Solvents," *J. Am. Chem. Soc.*, 109:3802-04 (1987).
*Miller et al., "Peroxide Modification of Monoalkylated Glutathione Reductase," *The Journal of Biological Chemistry*, 266:19342-19360 (1991).
*Moree et al., "Exploitation of Subtilisin BPN as Catalyst for the Synthesis of Peptides Containing Noncoded Amino Acids, Peptide Mimetics and Peptides Conjugates," *J. Am. Chem. Soc.*, 119:3942-47 (1997).
*Morihara et al., "α-Chymotrypsin as the Catalyst for Peptide Synthesis," *Biochem. J.*, 163:531-42 (1977).
*Nakatsuka et al., "Peptide Segment Coupling Catalyzed by the Semisynthetic Enzyme Thiolsubtilisin," *J. Am. Chem. Soc.*, 109:3808-10 (1987).
*Nakayama et al., "Chemical Modification of Cysteinyl, Lysyl and Histidyl Residues of Mouse Liver 17β-Hydroxysteroid Dehydrogenase," *Biochimica et Biophysica Acta*, 1120:144-150 (1992).
*Neet, K.E. and Koshland, D.E., "The Conversion of Serine at the Active Site of Subtilisin to Cysteine: A 'Chemical Mutation,'" *Proc. Nat. Acad. Sci. USA*, 56(5):1606-1611, (1966).
*Nishimura et al., "Reversible Modification of the Sulfhydryl Groups of *Escherichia coli* Succinic Thiokinase with Methanethiolating Reagents, 5,5'-Dithio-bis(2-Nitrobenzoic Acid), p-Hydroxymercuribenzoate, and Ethylmercurithiosalicylate," *Archives of Biochemistry and Biophysics*, 170:461-467 (1975).
*O'Connor et al., "Probing an Acyl Enzyme of Selenosubtilisin by Raman Spectroscopy," *J. Am. Chem. Soc.*, 118:239-240 (1996).
*Pardo et al., "Cysteine 532 and Cystein 545 Are the N-Ethylmaleimide-Reactive Residues of the *Neurospora* Plasma Membrane H+-ATPase," *The Journal of Biological Chemistry*, 264:9373-9379 (1989).
*Peterson et al., "Nonessential Active Site Residues Modulate Selenosubtilisin's Kinetic Mechanism," *Biochemistry*, 34:6616-6620 (1995).
*Peterson et al., "Selenosubtilisin's Peroxidase Activity Does Not Require an Intact Oxyanion Hole," *Tetrahedron*, 53:12311-12317 (1997).
*Planas et al., "Reengineering the Catalytic Lysine of Aspartate Aminotransferase by Chemical Elaboration of a Genetically Introduced Cysteine," *Biochemistry*, 30:8268-8276 (1991).
*Plettner, E., et al., "Modulation of Esterase and Amidase Activity of Subtilisin *Bacillus lentus* by Chemical Modification of Cysteine Mutants," *Journal of the American Chemical Society*, (Jun. 2, 1999) 121/21, 4977-4981, XPO000891274.
*Plettner, Erika et al., "A Combination Approach to Chemical Modification of Subtilisin *Bacillus lentus*," *Bioorganic & Medicinal Chemistry Letters* (Sep. 8, 1998) vol. 8, No. 17, pp. 2291-2296, XP0004138220.
*Polgar et al., "A New Enzyme Containing a Synthetically Formed Active Site. Thiol-Subtilisin," *Journal of American Chemical Society*, 88:3153-3154 (1966).
*Polgar, "Spectrophotometric Determination of Mercaptide Ion, an Activated Form of SH-Group in Thiol Enzymes," *FEBS Letters*, 38:187-190 (1974).
*Radziejewski et al., "Catalysis of N-Alkyl-1,4-Dihydronicotinamide Oxidation by a Flavopapain: Rapid Reaction in All Catalytic Steps," *J. Am. Chem. Soc.*, 107:3352-3354 (1985).
*Raia et al., "Activation of *Sulfolobus solfataricus* Alcohol Dehydrogenase by Modification of Cysteine Residue 38 with Iodoacetic Acid," *Biochemistry*, 35:638-647 (1996).
*Ramachandran et al., "Stabilization of Barstar by Chemical Modification of the Buried Cysteines," *Biochemistry*, 35:8776-8785 (1996).
*Roberts et al., "Reactivity of Small Thiolate Anions and Cysteine-25 in Papain Toward Methyl Methanethiosulfonate," *Biochemistry*, 25:5595-5601 (1986).
*Rokita et al., "Synthesis and Characterization of a New Semisynthetic Enzyme, Flavolysozyme," *J. Am. Chem. Soc.*, 108:4984-4987 (1986).

*Sears et al., "Engineering Enzymes for Bioorganic Synthesis. Peptide Bond Formation," *Biotechnolo. Prog.*, 12:423-33 (1996).
*Sears et al., "Engineering Subtilisin for Peptide Coupling: Studies on the Effects of Counterions and Site-Specificity Modifications on the Stability and Specificity of the Enzyme," *J. Am. Chem Soc.*, 116:6521-30 (1994).
*Siddiqui et al, "Arthrobacter D-Xylose Isomerase: Chemical Modification of Carboxy Groups and Protein Engineering Of pH Optimum," *Biochem. J.*, 295:685-691 (1993).
*Smith et al., "An Engineered Change in Substrate Specificity of Ribulosebisphosphate Carboxylase/Oxygenase," *The Journal of Biological Chemistry*, 265:1243-1245 (1990).
*Smith et al. "Chemical Modification of Active Site Residues in γ-Glutamyl Transpeptidase," *The Journal of Biological Chemistry*, 270:12476-12480 (1995).
*Smith et al., "Nonessentiality of the Active Sulfhydryl Group of Rabbit Muscle Creatine Kinase," *The Journal of Biological Chemistry*, 249:3317-3318 (1974).
*Smith et al., "Restoration of Activity to Catalytically Deficient Mutants of Ribulosebisphosphate Carboxylase/Oxygenase by Aminoethylation," *The Journal of Biological Chemistry*, 263:4921-4925 (1988).
*Smith et al., "Simple Alkanethiol Groups for Temporary Blocking of Sulfhydryl Groups of Enzymes," *Biochemistry*, 14:766-771 (1975).
*Smith et al., "Subtle Alteration of the Active Site of Ribulose Bisphosphate Carboxylase/Oxygenase by Concerted Site-Directed Mutagenesis and Chemical Modification," *Biochemical and Biophysical Research Communications*, 152:579-584 (1988).
*So et al., "Lipase-Catalyzed Synthesis of Peptides Containing D-Amino Acid," *Enzyme Microb. Technol.*, 23:211-15 (1998).
*Soper et al., "Effects of Substrates on the Selectie Modification of the Cysteinyl Residues of D-Aminio Acid Transaminase," *The Journal of Biological Chemistry*, 254:10901-10905 (1979).
*Spura, A., et al. Probing Agonist Domain of the Nicotinic Acetylcholine Receptor by Cysteine Scanning Mutogenesis Reveals Residues in Proximity to the Alpha-Bungarotoxin Binding Site, *Biochemistry*, Apr. 20, 1999 vol. 38:16 pp. 4912-4921.
*Stauffer et al., "Electrostatic Potential of the Acetylcholine Binding sites in the Nicotinic Receptor Probed by Reactions of Binding-Site Cysteines with Charged Methanethiosulfonates," *Biochemistry*, 33:6840-6849 (1994).
*Stepanov, "Proteinases as Catalysts in Peptide Synthesis," *Pure & Appl. Chem.*, 68(6):1335-39 (1996).
*Stewart et al., "Catalytic Oxidation of Dithiols by a Semisynthetic Enzyme," *J. Am. Chem. Soc.*, 108:3480-3483 (1986).
*Suckling et al., "Carbon-Carbon Bond Formation Mediated by Papain Chemically Modified by Thiazolium Salts," *Bioorganic & Medicinal Chemistry Letters*, 3:531-534 (1993).

*Svensson et al., "Mapping the Folding Intermediate of Human Carbonic Anhydrase II. Probing Substructure by Chemical Reactivity and Spin and Fluorescence Labelling of Engineered Cysteine Residues," *Biochemistry*, 34:8606-8620 (1995).
*Valenzuela et al., "Kinetic Properties of Succinylated and Ethylenediamine-Amidated δ-Chymotrypsins," *Biochim. Biophys. Acta*, 250:538-548 (1971).
*Watanabe, et al., "A Unique Enzyme from *Saccharothrix* sp. Catalyzing D-Amino Acid Transfer," *Biochimica et Biophysica Acta*, 1337:40-46 (1997).
*West et al., Enzyme-catalysed Synthesis of Peptides Containing D-Amino Acids, *J. Chem. Soc. Chem. Commun.*, pp. 417-18 (1986).
*West et al., "Enzyme-Catalyzed Irreversible Formation of Peptides Containing D-Amino Acids," *J. Org. Chem.*, 51:2728-35 (1986).
*West et al., "Enzymes as Synthetic Catalysts: Mechanistic and Active-Site Considerations of Natural and Modified Chymotrypsin," *J. Am. Chem. Soc.*, 112:5313-5320 (1990).
*West et al., "Modification of Proteases to Esterases for Peptide Synthesis: Methylchymotrypsin," *J. Am. Chem. Soc.*, 110:3709-10 (1988).
*White et al., "Sequential Site-Directed Mutagenesis and Chemical Modification to Convert the Active Site Arginine 292 Of Aspartate Aminotransferase to Homoarginine," *Journal of the American Chemical Society*, 114:292-293 (1992).
*Wong et al., "Enzymes in Organic Synthesis: use of Subtilisin and a Highly Stable Mutant Derived from Ultiple Site-Specific Mutations," *J. Am. Chem. Soc.*, 112:945-53 (1990).
*Worku et al., "Identification of Histidyl and Cysteinyl Residues Essential for Catalysis of 5'-Nucleotidase," *FEBS Letter*, 167:235-240 (1984).
*Wu et al., "Conversion of a Protease into an Acyl Transferase: Selenolsubtilisin," *J. Am. Chem. Soc.*, 111:4514-4515 (1989).
*Wynn et al., "Chemical Modification of Protein Thiols: Formation of Mixed Disulfides," *Methods in Enzymology*, 251:351-356 (1995).
*Wynn et al., "Comparison of Straight Chain and Cyclic Unnatural Amino Acids Embedded in the Core of Staphylococcal Nuclease," *Protein Science*, 6:1621-1626 (1997).
*Wynn et al., "Mobile Unnatural Amino Acid Side Chains in the Core of Staphylococcal Nuclease," *Protein Science*, 5:1026-1031 (1996).
*Wynn et al., "Unnatural Amino Acid Packing Mutants of *Escherichia coli* Thioredoxin Produced by Combined Mutagenesis/Chemical Modification Techniques," *Protein Science*, 2:395-403 (1993).
*Xu et al., "Amino Acids Lining the Channel of the γ-Am inobutyric Acid Type A Receptor Identified by Cysteine Substitution," *The Journal of Biological Chemistry*, 268:21505-21508 (1993).
*Zhang et al., Protease-catalyzed Small Peptide Synthesis in Organic Media, *Enzyme Microb. Technol.*, 19:538-44 (1996).

* cited by examiner

The corresponding (S) MTS ligands follow the same code scheme (i.e. (S)-a, (S)-b, (S)-d, (S)-e, (S)-f, (S)-g, (S)-h, (S)-i).

Reagents: (i) Me$_2$SO$_4$, NaOH, H$_2$O, 37%; (ii) MeOH, H$^+$; (iii) MOM-Cl, CH$_2$Cl$_2$, Et$_3$N (90% 2 steps); (iv) For (R)-3: BH$_3$, THF, 82%; For (R)-5 LiBH$_4$, THF, 97%; (v) MeSO$_2$Cl, CH$_2$Cl$_2$, Et$_3$N; For (R)-8: 100%; (vi) LiBr, acetone; For (R)-10: 84%; For (R)-11: 78% 2 steps; (vii) NaSSO$_2$CH$_3$, DMF; For (R)-12: 61%; (viii) TFA, H$_2$O, 82%.

Reagents: (i) KOH, DMSO, Br(CH$_2$)$_n$Br; (ii) NaSSO$_2$CH$_3$, DMF.

Reagents: (i) triphosgene, CH$_2$Cl$_2$, Et$_3$N, 100%;
(ii) KOH, DMSO, Br(CH$_2$)$_3$Br; (iii) NaSSO$_2$CH$_3$, DMF.

CHEMICALLY MODIFIED MUTANT SERINE HYDROLASES SHOW IMPROVED CATALYTIC ACTIVITY AND CHIRAL SELECTIVITY

CROSS-REFERENCE TO RELATED APPLICATIONS

This application is a continuation of U.S. application Ser. No. 10/791,093 filed Mar. 1, 2004, now abandoned, which is a continuation of U.S. application Ser. No. 09/436,513 filed Nov. 9, 1999, now abandoned, which claims the benefit under 35 U.S.C. §119, of U.S. Provisional Patent Application Ser. No. 60/107,758, filed on Nov. 10, 1998, now expired and Ser. No. 60/113,061 filed on Dec. 21, 1998, now expired, all of which are incorporated herein by reference in their entirety for all purposes.

STATEMENT AS TO RIGHTS TO INVENTIONS MADE UNDER FEDERALLY SPONSORED RESEARCH AND DEVELOPMENT

[Not Applicable]

BACKGROUND OF THE INVENTION

1. Field of the Invention

This invention pertains to the field of serine hydrolases. In particular, this invention pertains to serine hydrolases that have been mutated to introduce one or more cysteines which are then chemically derivatized. These chemically modified mutants demonstrate altered enzymatic activity.

2. Background

Enzymes are now widely accepted as useful catalysts in organic synthesis. However, natural wild-type enzymes do not accept all structures of synthetic chemical interest, nor do they always produce the desired (e.g. enantiomerically pure) products necessary for synthesis. This potential limitation of the synthetic applicabilities of enzymes has been recognized and some progress has been made in altering their specificities in a controlled manner, e.g. using site-directed and random mutagenesis techniques of protein engineering. However, modifying enzyme properties by protein engineering has been generally limited to making natural amino acid replacements. Although molecular biological strategies for overcoming this restriction have recently been derived (Cornish et al. (1995) *Angew. Chem. Int. Ed. Engl.*, 34: 621-633), these procedures are difficult to apply in most laboratories.

In contrast, controlled chemical modification of enzymes offers broad potential for facile and flexible modification of enzyme structure, thereby opening up extensive possibilities for controlled tailoring of enzyme specificity and activity. Changing enzyme properties by chemical modification has been explored previously with early reports by the groups of Bender (e.g. Polgar et al. (1966) *J. Am. Chem. Soc.*, 88: 3153-3154) and Koshland (see, e.g., Neet et al. (1966) *Proc. Natl. Acad. Sci., USA,* 56: 1606-1611) who created a thiosubtilisin by chemical transformation ($CH_2OH \rightarrow CH_2SH$) of the active site serine residue of subtilisin BPN' to cysteine.

Interest in chemically produced artificial enzymes, including some with synthetic potential was renewed by Wu (see, e.g., Wu et al. (1989) *J. Am. Chem. Soc.*, 111: 4514-4515), Bell et al. (1993) *Biochem.*, 32: 3754-3762), Peterson (see, e.g., Peterson et al. (1995) *Biochem.*, 34: 6616-6620), and more recently Suckling (see, e.g., Suckling et al. (1993) *Bioorg. Med. Chem. Lett.*, 3: 542-534).

U.S. Pat. No. 5,208,158 describes chemically modified detergent enzymes where one or more methionines have been mutated into cysteines. The cysteines are subsequently modified in order to confer upon the enzyme improved stability towards oxidative agents. Although improved stability is often a desirable property, it is also often desirable to alter other enzymatic properties (e.g. specificity, catalytic activity, stereoselectivity, etc.).

Many methods for improving the activity and enantioselectivity of hydrolases have been investigated. They include extreme temperatures (Noritomi et al. (1996) *Biotechnol. Bioeng.* 51: 95-99; Saka et al. (1997) *J. Org. Chem.* 62: 4906-4907; Ullmann et al. (1996) *Tetrahedron: Asymmetry* 7: 2047-2054; Holmberg et al. (1991) *Biotechnol. Lett.* 13: 323-326; Phillips (1992) *Enzyme Microb. Technol.* 14: 417-419; Lam et al. (1986) *J. Org. Chem.* 51: 2047-2050), solvent engineering (Koskinen et al. (1996) *Enzymatic Reactions in Organic Media,* A. M., Blackie Academic and Professional, London; Gutman et al. (1995) *Adv Biochem Eng/Biotechnol* 52: 87-128; Griebenow and Klibanov (1997) *Biotechnol. Bioeng.* 53: 351-362; Bonneau et al. (1993) *Bioorg. Chem.* 21: 431-438; structural variation of the substrate (Gupta and Kaslauskas (1993) *Tetrahedron: Asymmetry* 4: 879-888; Sih et al. (1992) *Chirality* 4: 91-97), imprinting (Rich and Dordick, (1997) *J. Am. Chem. Soc.* 119: 3245-3252; Russell and Klibanov (1988) *J. Biol. Chem.* 263: 11624-11626.), lyoprotectants (Dabulis and Klibanov (1993) *Biotechnol. Bioeng.* 41: 566-571; Khmelnitsky et al. (1994) *J. Am. Chem. Soc.* 116: 2647-2648), chemical modification (Scouten (1987) *Methods Enzymol.* 135: 30-78; Polgar and Bender (1966) *J. Am. Chem. Soc.* 88: 3153-3154; Wu and Hilvert, (1989) *Am. Chem. Soc.* 111: 4513-4514), site-directed mutagenesis (Wong et al. (1990) *J. Am. Chem. Soc.,* 112: 945-953; Bonneau et al. (1991) *J. Am. Chem. Soc.,* 113: 1026-1030; Zhong et al. (1991) *J. Am. Chem. Soc.* 113: 683-684; Estell et al. (1985) *J. Biol. Chem.* 260: 6518-6521; Sears and Wong (1996) *Biotechnol. Prog.,* 12: 423-433), and random mutagenesis (Reetz et al. (1997) *Angew. Chem. Int. Ed. Engl.* 36: 2830-2832; Chen and Arnold (1993) *Proc. Natl. Acad, Sci. USA,* 90: 5618-5622; Stemmer (1994) *Nature,* 370: 389-391). However, the chemical modification of mutant enzymes has been underused as a method for generating new hydrolases with novel properties (Gron et al. (1990) *Eur. J. Biochem.* 194: 897-901).

SUMMARY OF THE INVENTION

This invention provides unique chemically modified mutant enzymes (CMM) having improved stereoselectivity to a variety of substrates. In general, the mutants are serine hydrolases in which one or more amino acid residues (preferably residues in a subsite, e.g. $S_1$, $S_1$', or $S_2$) are replaced with a cysteine where the cysteine is chemically modified by replacing the thiol hydrogen in the cysteine with a substituent group providing a thiol side chain comprising a moiety selected from the group consisting of a polar aromatic substituent, an alkyl amino group with a positive charge, a chiral substituent, a heterocyclic substituent, and a glycoside. Preferred serine hydrolases of this invention catalyze a transamidation or a transpeptidation or a transesterification reaction and in a most preferred embodiment is stereoselective in this catalysis. Particularly preferred serine hydrolases include alpha/beta serine hydrolases, a subtilisin type serine proteases, and chymotrypsin serine proteases, with subtilisin being a particularly preferred serine protease.

Preferred amino acids selected for replacement with cysteine include asparagine, leucine, methionine, and serine.

Preferred sites for replacement (e.g. in subtilisin type enzymes) include amino acid 156 in the S1 subsite, amino acid 166 in the S1 subsite, amino acid 217 in the S1' subsite, amino acid 222 in S1' subsite and amino acid 62 in the S2 subsite, wherein these positions are numbered by correspondence with positions in the amino acid sequence of *Bacillus amyloliquefaciens* subtilisin. Preferred substituents include an oxazolidinone, a $C_1$ to $C_{15}$ alkyl amino group with a positive charge, and a glycoside (e.g., a monosaccharide, a disaccharide, and an oligosaccharide comprising pentoses and hexoses) (see, e.g., FIG. 2). In one embodiment, preferred substituents include (R)-2-methoxy-2-phenyl-ethyl-thiol, (S)-2-methoxy-2-phenyl-ethyl-thiol, (R)-2-hydroxy-2-phenyl-ethyl-thiol, (S)-2-hydroxy-2-phenyl-ethyl-thiol, N-(3'-thio-propyl)-2-oxazolidinone, N-(3'-thio-propyl)-(S)-4-phenyl-2-oxazolidinone, N-(3'-thio-propyl)-(R)-4-benzyl-2-oxazolidinone, N-(3'-thio-propyl)-(S)-4-benzyl-2-oxazolidinone, N-(2'-thio-ethyl)-(R)-4-phenyl-2-oxazolidinone, N-(2'-thio-ethyl)-(S)-4-phenyl-2-oxazolidinone, N-(2'-thioethyl)-(R)-4-benzyl-2-oxazolidinone, N-(2'-thio-ethyl)-(S)-4-benzyl-2-oxazolidinone, N-(3'-thio)-(3aR-cis)-3,3a,8,8a-tetrahydro-2H-indeno[1,2-d]-oxazol-2-one, and N-(3'-thio)-(3aS-cis)-3,3a,8,8a-tetrahydro-2H-indeno[1,2-d]-oxazol-2-one.

In another embodiment, this invention provides a chemically modified mutant subtilisin. The modified subtilisin has one or more amino acid residues selected from the S1, S1', or S2 subsites replaced with a cysteine, where the cysteine is modified by replacing the thiol hydrogen in the cysteine with a substituent group providing a thiol side chain comprising a moiety selected from the group consisting of a polar aromatic substituent, an alkyl amino group with a positive charge, an alkyl group bearing a negatively charged moiety, and a glycoside. Particularly preferred cysteine substitution(s) are at amino acid 62, amino acid 156, amino acid 166, amino acid 217, and amino acid 222, wherein these positions are numbered by correspondence with positions in the amino acid sequence of *Bacillus amyloliquefaciens* subtilisin. Preferred substituents are as described above and herein.

This invention also provides a method of forming a peptide bond. The methods preferably involve contacting a compound comprising an ester substrate with a serine hydrolase and/or a chemically modified mutant subtilisin as described herein and a primary amine under conditions whereby the hydrolase or modified subtilisin catalyzes the formation of a peptide bond. A preferred ester substrate is an acyl donor and a primary amine is an acyl acceptor (e.g. an amino acid amide). Where the acyl acceptor is an amino acid amide the amino acid can be a D or an L amino acid and can optionally be present in a peptide. The ester substrate can be a D or an L amino acid ester and can optionally be present in a peptide.

In still another embodiment, this invention provides methods of resolving racemic primary and secondary alcohols using a transesterification reaction. These methods involve contacting the racemic primary or secondary alcohol with a serine hydrolase and/or a modified mutant subtilisin as described herein and an acyl donor whereby said serine hydrolase catalyzes a transesterification reaction resolving the racemic primary or secondary alcohol. Preferred primary or secondary alcohols include, but are not limited to, an aliphatic alcohol, an aromatic alcohol, and a heterocyclic alcohol. Particularly preferred primary or secondary alcohols include, but are not limited to 2-phenyl-1-propanol, 2-methyl-1-pentanol, and 2 octanol. Preferred acyl donors include, but are not limited to carboxylic acid esters (e.g., including but not limited to alkyl, aralkyl such as benzyl, esters) and activated esters (e.g., mono-, and/or di-, and/or tri-haloalkyl).

Particularly preferred modified mutant enzymes include, but are not limited to L217C—$(CH_2)_2$—$SO_3^-$, N62C—$(CH_2)_2$—$SO_3^-$, and N62C—S—$CH_3$.

In still another embodiment this invention provides methods of attaching a chiral moiety to a substrate via a transamidation, a transesterification, or a transpeptidation reaction. These methods involve contacting a substrate (e.g., a peptide, an amino acid, etc.) having a reactive site suitable for a transesterification or a transamidation, and the moiety with a catalytic serine hydrolase as described herein whereby the chiral moiety is covalently coupled to the substrate. Preferred chiral moieties include, but are not limited to D amino acids, L-amino acids, acyclic aliphatics, a cyclic aliphatics, aralkyl R-carboxylic acids, aralkyl S-carboxylic acids, aromatic R-carboxylic acids, and aromatic S-carboxylic acids. In particularly preferred embodiments, the reaction is preferential for a moiety of one chirality. Particularly where the reaction is a transesterification the transesterification preferably results in an enantiomerically biased product.

This invention also provides methods of incorporating an amino acid into a polypeptide. These methods involve contacting an amino acid ester with a catalytic serine protease as described herein and an amino acid primary amine under conditions whereby the serine hydrolase catalyzes the formation of a peptide bond between the amino acid of the amino acid ester and the amino acid of the amino acid amine. Preferred amino acid esters are acyl donors and preferred amino acid amines are acyl acceptor(s). The amino acid amide can be a D or an L amino acid amide and may optionally be present in a peptide. Similarly, the amino acid ester may be a D or an L amino acid ester and may optionally be present in a peptide.

Also provided are methods of producing a chemically modified mutated serine hydrolase. These methods preferably involve providing a serine hydrolase wherein one or more amino acids have been replaced with cysteine residues; and replacing the thiol hydrogens in the cysteine residues with a substituent group providing a thiol side chain comprising a moiety selected from the group consisting of a polar aromatic substituent, an alkyl amino group with a positive charge, and a glycoside. Particularly preferred hydrolases include, but are not limited to alpha/beta serine proteases, subtilisin type serine proteases, and chymotrypsin serine proteases with subtilisins being most preferred serine hydrolases. The amino acid replaced with a cysteine preferably amino acid in the S1, S1', or S2 subsite (e.g., subtilisin residues 156, 166, 217, 222, and 62, wherein these positions are numbered by correspondence with positions in the amino acid sequence of *Bacillus amyloliquefaciens* subtilisin) and/or preferably an asparagine, a leucine, a methionine, and a serine. Particularly preferred substituents are as described herein. The methods may further involve screening the modified serine hydrolase for an activity selected from the group consisting of a transesterification activity, a transamidation activity, and a transpeptidation activity. The screens may optionally include a screen for stereoselectivity.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term may also include variants on the traditional peptide linkage joining the amino acids making up the polypeptide.

The term "residue" as used herein refers to natural, synthetic, or modified amino acids.

The terms enzyme includes proteins that are capable of catalyzing chemical changes in other substances without being permanently changed themselves. The enzymes can be wild-type enzymes or variant enzymes. Enzymes within the scope of the present invention include, but are not limited to, pullulanases, proteases, cellulases, amylases, isomerases, lipases, oxidases, oxidoreductases, hydrolases, aldolases, ketolases, glycosidases, lyases, transferases, and ligases.

A "mutant enzyme" is an enzyme that has been changed by replacing an amino acid residue with a cysteine (or other) residue.

A "chemically modified" enzyme is an enzyme that has been derivatized to bear a substituent not normally found at that location in the enzyme.

A "chemically modified mutant enzyme" or "CMM" is an enzyme in which an amino acid residue has been replaced with another amino acid residue (preferably a cysteine) and the replacement residue is chemically derivatized to bear a substituent not normally found on that residue.

The term "thiol side chain group", "thiol containing group", and thiol side chain" are terms that can be used interchangeably and include groups that are used to replace the thiol hydrogen of a cysteine. Commonly the thiol side chain group includes a sulfur atom through which the thiol side chain group is attached to the thiol sulfur of the cysteine. The "substituent" typically refers to the group that remains attached to the cysteine through a disulfide linkage formed by reacting the cysteine with a methanesulfonate reagent as described herein. While the term substituent preferably refers just to the group that remains attached (excluding its thiol group), the substituent can also refer to the entire thiol side chain group. The difference will be clear from the context.

The "binding site of an enzyme" consists of a series of subsites across the surface of the enzyme. The substrate residues that correspond to the subsites are labeled P and the subsites are labeled S. By convention, the subsites are labeled $S_1$, $S_2$, $S_3$, $S_4$, $S_1'$, and $S_2'$. A discussion of subsites can be found in Siezen et al. (1991) *Protein Engineering*, 4: 719-737, and Fersht (1985) *Enzyme Structure and Mechanism*, 2nd ed. Freeman, New York, 29-30. The preferred subsites include $S_1$, $S_1'$, and $S_2$.

The terms "stereoselectivity" or "stereoselective" when used in reference to an enzyme or to a reaction catalyzed by an enzyme refers to a bias in the amount or concentration of reaction products in favor of enantiomers of one chirality. Thus a stereoselective reaction or enzyme will produce reaction products that predominate in the "D" form over the "L" form (or "R" form over the "S" form) or conversely that predominate in the "L" form over the "D" form (or "S" form over the "R" form). The predominance of one chirality is preferably a detectable predominance, more preferably a substantial predominance, and most preferably a statistically significant predominance (e.g. at a confidence level of at least 80%, preferably at least 90%, more preferably at least 95%, and most preferably at least 98%).

The phrase "amino acid ##" or "amino acid ## in the XX subsite" is intended to include the amino acid at the referenced position (e.g. amino acid position 156 of *B. lentus* subtilisin which is in the $S_1$ subsite) and the amino acids at the corresponding (homologous) position in related enzymes.

A "serine hydrolase" is a hydrolytic enzyme utilizing an active serine side chain to serve as a nucleophile in a hydrolytic reaction. This term includes native and synthetic serine hydrolases as well as enzymes engineered to perform the reverse reaction, e.g., for synthetic purposes.

The "alpha/beta serine hydrolases" are a family of serine hydrolyases based on structural homology to enzymes including wheat germ serine carboxypeptidase II (see, e.g., Liao et al. (1992) *Biochemistry* 31: 9796-9812; Ollis et al. (1992) *Protein Engineering*, 5: 197-211).

The "subtilisin type serine proteases" refer to a family of serine hydrolyases based on structural homology to enzymes in including subtilisin BPN' (Bott et al. (1988) *J. Biol. Chem.* 263: 7895-7906; Siezen and Leunissen (1997) *Protein Science* 6: 501-523). Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases.

The "chymotrypsin serine protease family" refers to a family of serine hydrolyases based on structural homology to enzymes including gamma chymotrypsin (Birktoft and Blow (1972) *J. Molecular Biology* 68: 187-240).

The term "oxazolidinone" refers to a compound including an oxazolidine ring and containing a keto group.

The term "glycoside" refers to a group of organic compounds that can be resolved by hydrolysis into sugars and other organic substances (e.g. aglycones). Preferred glycosides are acetals that are derived from a combination of various hydroxy compounds with various sugars. They may be designated individually as glucosides, mannosides, galactosides, etc. Preferred glycosides include, but are not limited to monosachamides and oligosaccharides, including pentose and hexose saccharides, including glucose and mannose containing saccharides.

Resolving a recemic mixture refers to racemic primary and secondary alcohols resolving racemic primary and secondary alcohols

DETAILED DESCRIPTION

Figure 1:
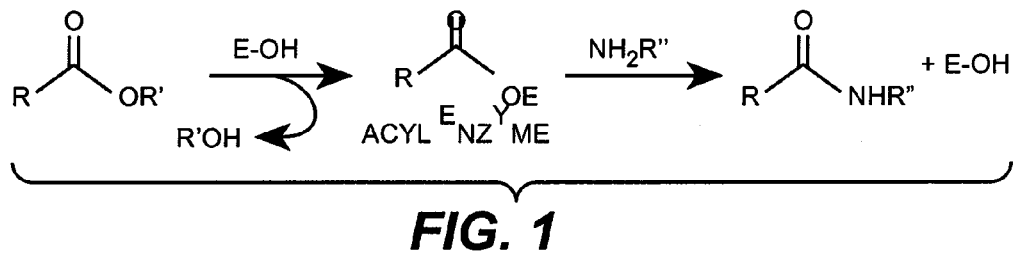
FIG. 1 illustrates peptide coupling catalyzed by an enzyme.

This invention provides chemically modified mutant enzymes (CMMs) that are capable of catalyzing transesterification and/or transamidation and/or transpeptidation reactions. Preferred modified enzymes of this invention maintain a high degree of stereoselectivity in the reaction.

The chemically modified mutant enzymes of this invention comprise a serine hydrolase in which one or more residues in one or more subsite(s) are mutated to a cysteine and the cysteine is derivatized (e.g. with a methanesulfonate reagent) to provide a substituent coupled in place of the thiol hydrogen on the cysteine. The site(s) of mutation and the substituents are selected to produce an enzyme that maintains a higher degree of stereoselectivity than the wild type enzyme in a transesterification, transamidation, or transpeptidation reaction.

The mutant enzymes are useful in a wide variety of contexts including, but not limited to peptide synthesis, transesterification, resolution of enantiomers via stereoselective catalysis of racemic esters or amides and related groups, detergents and other cleaning materials, textile treatments, feed additives, and the like. Because of their stereoselectivity, the mutant enzymes are particularly useful as reagents that catalyze steps in organic syntheses. If desired, the mutant enzymes produce an enantiomerically purer reaction product and, in certain preferred embodiments, can be used to catalyze reactions that are otherwise difficult. Thus, for example, in one embodiment the enzymes can be used to catalyze a transamidation reaction where a "D" amino acid is coupled to an "L" amino acid. To facilitate such transamidation reactions, in certain preferred embodiment, the modified enzyme has high esterase and low amidase activity.

I. Production of Mutant Enzymes for Chemical Modification.

A) Selection of Enzymes for Modification.

Preferred enzymes for modification according to this invention include the serine hydrolases. The serine hydrolases are a class of hydrolytic enzymes characterized by a hydrolytic enzymes that possess a catalytic triad composed of a serine, histidine and a carboxylate amino acid (either aspartic or glutamic acid), and which catalyze the hydrolysis, and microscopic reverse reactions thereof, of carboxylic acid derivatives including, but not restricted to, esters, peptides and amides.

Preferred serine hydrolases comprising this invention include the trypsin-chymotrypsin proteases, the subtilisin proteases, and the alpha/beta hydrolases. In a particularly preferred embodiment the enzyme is protease, more preferably a subtilisin (e.g. a *Bacillus lentus* subtilisin). The subtilisins are alkaline serine proteases that are finding increasing use in biocatalysis, particularly in chiral resolution, regioselective acylation of polyfunctional compounds, peptide coupling, and glycopeptide synthesis. The latter two applications are of particular interest because they provide an alternative to site-directed mutagenesis for introducing unnatural amino acids into proteins.

Other particularly preferred serine hydrolases for use in this invention include, but are not limited to all serine hydrolases including enzymes that belong to the subtilisin class (subtilases), $\alpha\beta$ hydrolases or trypsin/chymotrypsin families of structurally serine hydrolase enzymes.

B) Selection of Residues for Modification.

In a preferred embodiment, residues for modification in the serine hydrolase are rationally selected. Particularly preferred amino acid residues selected for modification include residues expected to be important discriminatory sites within the subsites. Such resides are determined from mutagenesis experiments where the subsite residues are systematically mutagenized and the effect of such mutagenesis on binding specificity and/or enzymatic activity is determined. In addition, important residues can be identified from inspection of crystal structures and/or from predicted protein folding or protein-protein interactions determined using protein modeling software (e.g., Quanta Molecular Simulations Inc.) and Frodo (academic software). Side chains situated to alter interaction at subsites defined by Berger and Schecter can be selected based on the crystallographic models of the enzymes and extrapolated to homologous enzymes if necessary if structural information on a specfic enzyme is unavailable. In *B. lentus* subtilisin sites 156, 166, 217 and 222 are important substrate specificity determining sites, wherein these positions are numbered by correspondence with positions in the amino acid sequence of *Bacillus amyloliquefaciens* subtilisin. These along with site 62 identified specifically for this study are exemplified. Additional related sites include position 96, 104, 107, 189 and 209 in subtilisin and homologous positions in related enzymes, wherein these positions are numbered by correspondence with positions in the amino acid sequence of *Bacillus amyloliquefaciens* subtilisin.

Typically residues are selected where introduction of a substituent, which can be, but is not restricted to being, small, bulky, hydrophobic or hydrophilic, or charged, is expected to change the conformation of the binding site. In preferred embodiments, such residues typically lie in the S1, S1', or S2 subsites although it will be appreciated that in certain cases, alteration of residues in other subsites can also produce dramatic effects.

In one particularly preferred embodiment, where the serine hydrolase is a subtilisin-type serine hydrolase, preferred residues for mutation include, but are not limited to residues 156 and 166 in the S1 subsite, residues 217 and 222 in the S1' subsite and residue 62 in the S2 subsite Leu96, Val104, Ile107, Phe189 and Tyr209 or residues at homologous positions within the subsites of other subtilisin-type serine proteases, wherein these positions are numbered by correspondence with positions in the amino acid sequence of *Bacillus amyloliquefaciens* subtilisin.

In another preferred embodiment, where the serine hydrolase is a trypsin-chymotrypsin type serine hydrolase, preferred residues for mutation include Tyr94, Leu99, Gln175, Asp189, Ser190 and Gln192 of trypsin or residues at homologous positions within the subsites of other trypsin-chymotrypsin-type serine proteases, wherein these positions are numbered by correspondence with positions in the amino acid sequence of *Bacillus amyloliquefaciens* subtilisin.

In still another preferred embodiment, where the serine hydrolase is an alpha/beta serine hydrolase, preferred residues for mutation include Trp104, Thr138, Leu144, Val154, Ile189, Ala 225, Leu278 and Ile185 of *Candida antartica* lipase (Protein Data Bank entry 1tca) or residues at homologous positions within the subsites of other alpha/beta type serine hydrolases, wherein these positions are numbered by correspondence with positions in the amino acid sequence of *Bacillus amyloliquefaciens* subtilisin.

Preferably the amino acids replaced in the enzyme by cysteines are selected from the group consisting of asparagine, leucine, methionine, or serine. More preferably the amino acid to be replaced is located in a subsite of the enzyme preferably the S1, S1' or S2 subsites. More preferably, in a subtilisin the amino acids to be replaced are N62, L217, M222, S156, S166, site 104, site 107 (S4), site 96 (S2), site 189 (S2'), and site 209 (S1'/S3') or their homologues where the numbered position corresponds to naturally occurring subtilisin from *Bacillus amyloliquefacients* or to equivalent amino acid residues in other subtilisins such as *Bacillus lentus* subtilisin, wherein these positions are numbered by correspondence with positions in the amino acid sequence of *Bacillus amyloliquefaciens* subtilisin.

C) Introduction of Cysteine.

The substitution of a cysteine for one or more native residue(s) in the serine hydrolase can be accomplished using routine methods well known to those of ordinary skill in the art. In one preferred embodiment, the mutants described herein are most efficiently prepared by site-directed mutagenesis of the DNA encoding the wild-type enzyme of interest (e.g. *Bacillus lentis* subtilisin). Techniques for performing site-directed mutagenesis or non-random mutagenesis are known in the art. Such methods include, but are not limited to alanine scanning mutagenesis (Cunningham and Wells (1989) *Science,* 244, 1081-1085), oligonucleotide-mediated mutagenesis (Adellman et al. (1983) *DNA,* 2, 183), cassette mutagenesis (Wells et al. (1985) *Gene,* 344: 315) and binding mutagenesis (Ladner et al. WO 88/06630).

In one embodiment of the present invention, the substitute amino acid residue (e.g. cysteine) is introduced to the selected target site by oligonucleotide-mediated mutagenesis using the polymerase chain reaction technique. In this approach, the gene encoding the desired native enzyme (e.g. subtilisin) is carried by a suitable plasmid. More preferably, the plasmid is an expression vector, e.g., a plasmid from the pBR, pUC, pUB, pET or pHY4 series. The plasmid can be chosen by persons skilled in the art for convenience or as desired.

For site-directed mutagenesis, the fragment containing the selected mutation site is cleaved from the gene encoding the subject enzyme by restriction endonucleases and is used as the template in a modified PCR technique (see, Higuchi et al. (1988) *Nucleic Acid Res.,* 16, 7351-7367). For each target substitution, an oligonucleotide containing the desired mutation is used as a mismatch primer to initiate chain extension between 5' and 3 PCR flanking primers. The process includes two PCR reactions. In the first PCR, the mismatch primer and the 5' primer are used to generate a DNA fragment containing the desired base substitution. The fragment is separated from the primers by electrophoresis. After purification, it is then used as the new 5' primer in a second PCR with the 3' primer to generate the complete fragment containing the desired base substitution. After confirmation of the mutation by sequencing, the mutant fragment is then inserted back to the position of the original fragment.

In another approach, a cassette mutagenesis method may be used to facilitate the construction and identification of the cysteine mutants of the present invention. First, the gene encoding the serine hydrolase is obtained and sequenced in whole or in part. Then the point(s) at which it is desired to make a mutation of one or more amino acids in the expressed enzyme are identified. The sequences flanking these points are evaluated for the presence of restriction sites for replacing a short segment of the gene with an oligonucleotide which when expressed will encode the desired mutants. Such restriction sites are preferably unique sites within the serine hydrolase gene so as to facilitate the replacement of the gene segment. However, any convenient restriction site which is not overly redundant in the hydrolase gene may be used, provided the gene fragments generated by restriction digestion can be reassembled in proper sequence. If restriction sites are not present at locations within a convenient distance from the selected point (e.g., from 10 to 15 nucleotides), such sites are generated by substituting nucleotides in the gene in such a fashion that neither the reading frame nor the amino acids encoded are changed in the final construction. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Mutation of the gene in order to change its sequence to conform to the desired sequence is accomplished e.g., M13 primer extension in accord with generally known methods. Once the gene is cloned, the restriction sites flanking the sequence to be mutated are digested with the cognate restriction enzymes and the end termini-complementary oligonucleotide cassette(s) are ligated into the gene. The mutagenesis is enormously simplified by this method because all of the oligonucleotides can be synthesized so as to have the same restriction sites, and no synthetic linkers are necessary to create the restriction sites.

A suitable DNA sequence computer search program simplifies the task of finding potential 5' and 3' convenient flanking sites. In preferred embodiments, any mutation introduced in creation of the restriction site(s) are silent to the final construction amino acid coding sequence. For a candidate restriction site 5' to the target codon a sequence preferably exists in the gene that contains at least all the nucleotides but for one in the recognition sequence 5' to the cut of the candidate enzyme. For example, the blunt cutting enzyme SmaI (CCC/GGG) would be a good 5' candidate if a nearby 5' sequence contained NCC, CNC, or CCN. Furthermore, if N needed to be altered to C this alteration preferably leaves the amino acid coding sequence intact. In cases where a permanent silent mutation is necessary to introduce a restriction site one may want to avoid the introduction of a rarely used codon. A similar situation of SmaI would apply for 3' flanking sites except the sequence NGG, GNG, or GGN must exist. The criteria for locating candidate enzymes is most relaxed for blunt cutting enzymes and most stringent for 4 base overhang enzymes. In general many candidate sites are available.

A particularly preferred of method of introducing cysteine mutants into the enzyme of interest is illustrated with respect to the subtilisin gene from *Bacillus lentus* ("SBL"). In a preferred embodiment, the gene for SBL is cloned into a bacteriophage vector (e.g. M13 mp 19 vector) for mutagenesis (see, e.g. U.S. Pat. No. 5,185,258). Oligonucleotide-directed mutagenesis is performed according to the method described by Zoller et al. (1983) *Meth. Enzymol.,* 100: 468-500. The mutated sequence is then cloned, excised, and reintroduced into an expression plasmid (e.g. plasmid GG274) in the *B. subtilis* host. PEG (50%) is added as a stabilizer.

The crude protein concentrate thus obtained is purified by first passing through a Sephadex™ G-25 desalting matrix with a pH 5.2 buffer (e.g. 20 mM sodium acetate, 5 mM $CaCl_2$) to remove small molecular weight contaminants. Pooled fractions from the desalting column are then applied to a strong cation exchange column (e.g. SP Sepharose™ FF) in the sodium acetate buffer described above and the SBL is eluted with a one step gradient of 0-200 mM NaCl acetate buffer, pH 5.2. Salt-free enzyme powder is obtained following dialysis of the eluent against Millipore purified water and subsequent lyophilization.

The purity of the mutant and wild-type enzymes, which are denatured by incubation with a 0.1 M HCl at 0° C. for 30 minutes is ascertained by SDS-PAGE on homogeneous gels (e.g. using the Phast™ system from Pharmacia, Uppsala, Sweden). The concentration of SBL is determined using the Bio-Rad (Hercules, Calif.) dye reagent kit which is based on the method of Bradford (1976) *Anal. Biochem.*, 72: 248-254). Specific activity of the enzymes is determined as described below and in the examples.

One of ordinary skill in the art will appreciate that the protocol described above can be routinely modified, if necessary, for use with other enzymes. Other protocols for site-directed modification of proteins are well know to those of skill in the art and can be found, for example, in U.S. Pat. Nos. 5,932,419 and 5,789,166 Circular site-directed mutagenesis, 5,705,479 and 5,635,475 Site-directed mutagenesis modified glycoprotein hormones and methods of use, 5 5,556,747 Method for site-directed mutagenesis, 5,354,670 Site-directed mutagenesis of DNA, 5,352,779, Site-directed mutagenesis modified DNA encoding glycoprotein hormones and methods of use, 5,284,760 Techniques for producing site-directed mutagenesis of cloned DNA, and 5,071,743 Process for conducting site-directed mutagenesis.

In addition, kits for site-directed mutagenesis are commercially available (see, e.g. Transfomer™ Site-Directed Mutagenesis Kit available from Toyobo).

D) Expression of the Mutated Enzyme.

In a preferred embodiment, the mutated protein is expressed from a heterologous nucleic acid in a host cell. The expressed protein is then isolated and, if necessary, purified. The choice of host cell and expression vectors will to a large extent depend upon the enzyme of choice and its source.

A useful expression vector contains an element that permits stable integration of the vector into the host cell genome or autonomous replication of the vector in a host cell independent of the genome of the host cell, and preferably one or more phenotypic markers that permit easy selection of transformed host cells. The expression vector may also include control sequences encoding a promoter, ribosome binding site, translation initiation signal, and, optionally, a repressor gene, a selectable marker or various activator genes. To permit the secretion of the expressed protein, nucleotides encoding a signal sequence may be inserted prior to the coding sequence of the gene. For expression under the direction of control sequences, a gene or cDNA encoding a mutated enzyme to be used according to the invention is operably linked to the control sequences in the proper reading frame.

Vectors containing the mutant genes obtained by site-directed mutagenesis are then used respectively to transform suitable host cells and expressed. Suitable host cells include bacteria such as *E. coli* or *Bacillus*, yeast such as *S. cerevisiae*, mammalian cells such as mouse fibroblast cell, or insect cells. Preferably, a bacterial expression system is used. Most preferably, the host is *Bacillus*. Protein expression is performed by processes well known in the art according to factors such as the selected host cell and the expression vector to culture the transformed host cell under conditions favorable for a high-level expression of the foreign plasmid.

Methods of cloning and expression of peptides are well known to those of skill in the art. See, for example, Sambrook, et al. (1989) *Molecular Cloning: a Laboratory Manual* (2nd Ed., Vols. 1-3, Cold Spring Harbor Laboratory), Berger and Kimmel (1987) *Methods in Enzymology*, Vol. 152: *Guide to Molecular Cloning Techniques*, Academic Press, Inc. San Diego, or Ausubel et al. (1987) *Current Protocols in Molecular Biology*, Greene Publishing and Wiley-Interscience, New York.

As indicated above, one particularly preferred expression system is plasmid GG274 which is then expressed in a *B. subtilis* host.

II. Chemical Modification of Mutant Enzyme.

A) Selection of Substituents for Modifying Mutated Residues.

A wide variety of substituents can be used to modify the cysteine(s) introduced into the serine hydrolase. As indicated above, preferred substituents are those that improve stereoselectivity of the enzyme in a transesterification and/or a transamidation and/or a transpeptidation reaction. Preferred substituents are bulky (e.g. at least about 4-6 angstroms in one dimension and/or consisting of three of more atoms in a linear, cyclic or branched conformation), and/or hydrophobic, and/or charged.

In more preferred embodiments, the substituents include polar aromatic groups (e.g. derivatized benzenes such as fluorobenzene, chlorobenzene, derivatized 5 member rings, oxazolidadones, etc.). Other preferred substituents include alkyl amino groups with a positive charge (e.g. $C_1$ to $C_{50}$, more preferably $C_1$ to $C_{30}$ and most preferably $C_1$ to $C_{15}$ alkyl amino groups with a positive charge) and glycosides (e.g. mono or oligosacchamides derived from pentoses and hexoses and derivatives thereof). Where transesterification activity is desired, particularly preferred embodiments include alkyl groups (e.g. $C_1$ to $C_{50}$, more preferably $C_1$ to $C_{30}$ and most preferably $C_1$ to $C_{15}$ alkyl groups) bearing a negative charge (e.g. $SO_3^-$, and other sulfur acids, $CO_2^-$, and other acidic species including phopsphorus acid moieties, etc.).

Where transamidation or transpeptidation activity is desired and/or where a high degree of chiral specificity is desired, particularly preferred substituents include polar aromatic groups, with oxazolidinones being most preferred. Typical oxazolidinones for use in this invention include, but are not limited to, (R)-2-methoxy-2-phenyl-ethyl-thiol, (S)-2-methoxy-2-phenyl-ethyl-thiol, (R)-2-hydroxy-2-phenyl-ethyl-thiol, (S)-2-hydroxy-2-phenyl-ethyl-thiol, N-(3'-thio-propyl)-2-oxazolidinone, N-(3'-thio-propyl)-(S)-4-phenyl-2-oxazolidinone, N-(3'-thio-propyl)-(R)-4-benzyl-2-oxazolidinone, N-(3'-thio-propyl)-(S)-4-benzyl-2-oxazolidinone, N-(2'-thio-ethyl)-(R)-4-phenyl-2-oxazolidinone, N-(2'-thio-ethyl)-(S)-4-phenyl-2-oxazolidinone, N-(2'-thioethyl)-(R)-4-benzyl-2-oxazolidinone, N-(2'-thio-ethyl)-(S)-4-benzyl-2-oxazolidinone, N-(3'-thio)-(3aR-cis)-3,3a,8,8a-tetrahydro-2H-indeno[1,2-d]-oxazol-2-one, and N-(3'-thio)-(3aS-cis)-3,3a,8,8a-tetrahydro-2H-indeno[1,2-d]-oxazol-2-one.

Figure 2:
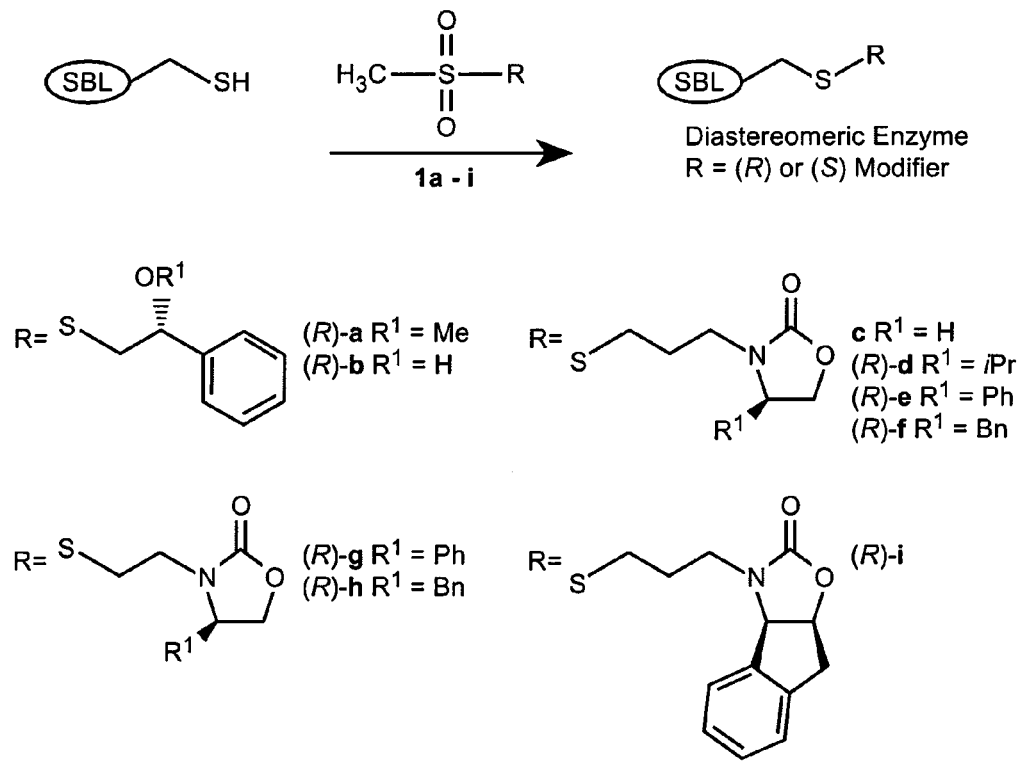
FIG. 2 illustrates synthesis scheme 1; the modification of SBL mutants with chiral auxiliaries.

Other particularly preferred embodiments include, but are not limited to, the substituents illustrated in FIG. 2 and other particularly preferred embodiments include, but are not limited to, the substituents illustrated in FIG. 2 and any of the commonly available chiral auxiliaries and ligands applied in asymmetric synthesis.

B) Coupling Substituents to the Cysteine.

The R group on cysteines provides a convenient relatively reactive thiol group (—SH) that can be exploited for coupling a desired substituent to the cysteine. In a preferred embodiment, the substituent of interest is provided, derivatized as a methanethiosulfonate reagent which, when reacted with the cysteine, results in the substituent of interest covalently coupled to the cysteine by a disulfide linkage (—S—S—).

In a preferred embodiment, chemical modification with the methanethiosulfonate reagent(s) is carried out as described by Berglund et al. (1997) *J. Am. Chem. Soc.*, 119: 5265-5255 and DeSantis et al. (1998) *Biochemistry*, 37: 5968-5973. Briefly, 200 μL of a 1 M solution of the methanethiosulfonate (MTS) reagent is added to a solution (5-10 mg/mL, 3.5 mL) of the cysteine mutant in 70 mM CHES, 5 mM MES, 2 mM CaCl$_2$, pH 9.5. The MTS reagent is added in two portions over 30 minutes. Reaction mixtures are kept at 20° C. with continuous end-over-end mixing. Reactions are monitored by following the specific activity (e.g. with suc-AAPF-pNA) and by tests for residual free thiol (e.g. with Ellman's reagent). Once the reaction is complete, the reaction mixture is loaded on a Sephadex™ PD-10 G25 column with 5 mM MES and 2 mM CaCl$_2$, pH 6.5. The protein fraction is then dialyzed against 1 mM CaCl2 and the dialysate is lyophilized.

In certain instances, where the substituent that is to be coupled to the cysteine, bears reactive groups the reactive groups may be derivatized with appropriate blocking/protecting groups to prevent undesired reactions during the coupling. Similarly, where the serine hydrolase contains one or more cysteines that are not to be derivatized, the thiol group(s) on these cysteines may be derivatized with appropriate protecting groups (e.g. (e.g. benzyl, trityl, tert-butyl, MOM, acetyl, thiocarbonate, thiocarbamate, and others). The use of blocking/protecting groups is well know to those of skill in the art (see, e.g., *Protective Groups in Organic Synthesis* Theodora W. Greene and Peter G. M. Wuts Third Edition, Wiley-Interscience, Toronto, (1999), pp 454-493.)

III. Screening Chemically Modified Mutants for Desired Activity.

The chemically modified mutants are typically screened for the activity or activities of interest. Such activities include amidase activity, esterase activity, the ratio of amidase to esterase activity, stereoselectivity, transesterification, transamidation, transpeptidation, and the like. Assays for such activities are well known to those of skill in the art.

For example, assays for amidase and/or esterase activity can be rapidly performed on microtiter plates as described by Plettner et al. (1998) *Bioorg. Med. Chem. Lett*, 8: 2291-2296. In one preferred embodiment, $k_{cat}/K_M$ is obtained in a microtiter plate format, from the rate of product formation (v) using the limiting case of the Michaelis-Menten equation at low substrate concentration as an approximation (Equation 1 where [S] and [E] are the substrate and enzyme concentrations, respectively): $V \approx (K_{cat}/K_M)[S][E]$ for $[S]<<K_M$ Enzyme stock solutions are prepared in 5 mM 4-morpholineethanesulfonic acid (MES) with 2 mM CaCl$_2$, pH 6.5 at about $5 \times 10^{-7}$ M for amidase and about $5 \times 10^{-8}$ M for esterase assays. Substrate solutions are prepared in dimethyl sulfoxide (DMSO). The amidase substrate sucAAPF-pNa stock is 1.6 mM which give s 0.8 mM in the well. The esterase substrate isosuccinyl-alanine-alanine-proline-phenylalanine-thiobenzyl ester (sucAAPF-SBn) stock solution is 1.0 mM, which gives 0.05 mM in the well. Assays are carried out in 0.1 M tris hydroxymethylaminomethane (Tris) pH 8.6 with 0.005% Tween. Tris buffer for the esterase assay contains 0.375 nM DTNB. This buffer should be used immediately as the DTNB decomposes within a few hours due to the high pH of the buffer.

A sample of each enzyme solution (~150 μL) is placed in a well in the 1st, 5th, or 9th column of an enzyme loading plate. Rows A to G contain enzymes, and row H contains MES buffer. On a separate assay plate (Corning, flat bottom, 96-well), 10 μL of substrate solution and 180 μL of buffer are dispensed into wells along columns to be used in a run. Columns 1-4 on the assay plate contain four replicates of the enzymes in column 1 of the loading plate; columns 5-8 contain four replicates of the enzymes in column 5 of the loading plate.

Reactions are initiated by transferring 10 μL of enzyme solution from the loading plate to the assay plate with an 8-channel pipette. For amidase assays, four columns are initiated for one run. For esterase assays, two columns are initiated for a run. The time delay between addition of enzyme to the first column and onset of reading is about 22-30 seconds (amidase) and 10-15 seconds (esterase). Immediately after initiation the pate is placed on a Titertech Multiscan MCC340 reader (programmed in the kinetic mode, filter 414 nm, lag time 0.0 minutes, interval 5 seconds with automatic background subtraction of blank row H) (Labsystems, Finland) and is read for 1.0 minute (amidase) or 30 seconds (esterase). Prolonged reading, past the nearly linear part of the progress curve) up to ~50% conversion) provides an underestimate of the rate. The output from the reader represents the average rate of change in absorbance at 414 nm min$^{-1}$, measured at 5 second intervals, of the total time programmed. These data are converted to rates in MS$^{-1}$ using the extinction coefficients for p-nitroanilide and for 3-carboxylate-4-nitrothiophenolate (e.g., $e_{414}$=8581 M$^{-1}$cm$^{-1}$ for p-nitroanilide and $e_{414}$=8708M$^{-1}$ cm$^{-1}$). Both extinction coefficients are determined on the reader using the same conditions and background subtraction as in the assay. The rates are corrected for active enzyme concentration and the four replicates for each enzyme are averaged.

It will be appreciated that the foregoing protocol is exemplary and not limiting and numerous modifications and variants can be performed with only routine experimentation by one of ordinary skill in the art.

In certain embodiments, other catalytic activities are assayed (e.g. transamidation, transpeptidation, transesterification). In addition, in certain embodiments, substrate specificity and/or stereoselectivity is also determined.

Such assays can be performed using routine methods. Thus, for example, transesterification or transamidation activities can be determined as described in the examples. Similarly stereoselectivity can be determined according to a number of methods known to those of skill in the art. In one embodiment, stereoselectivity is determined by using stereoselective liquid or gas chromatographic procedures (e.g., using Chiralcel columns, Daicel Chemical Industries, Ltd.) as described in the examples.

Production of chemically modified mutant enzymes and screening for particular activities of such modified enzymes is amenable to high throughput methodologies. Typically such methodologies utilize robotics to automate and speed the production and screening of large numbers of compounds. In efficient high throughput screening system, typically hundreds of thousands of reactants/reactions can be screened in a few days with only routine operator involvement. High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.).

These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

IV. Uses of the CMMs of this Invention.

As shown in FIG. 1, subtilisins can catalyze peptide bond formation starting from an ester substrate, by first forming an acyl enzyme intermediate which then reacts with a primary amine to form the peptide product. In this embodiment, preferred enzymes have high esterase activity to promote acyl enzyme formation and then low amidase activity to minimize hydrolysis of the peptide bond of the desired product. Generally subtilisins do not meet this requirement and in one embodiment the improvement of the esterase to amidase selectivities of subtilisins is one feature of the present invention.

Another particularly preferred feature of this invention, is the improved stereoselectivity obtained with the modified mutant enzymes. As indicated in the Examples the modified mutant enzymes can be utilized to resolve racemic alcohols and to stereoselectively acylate prochiral and meso diols.

The stereoselective modified enzymes of this invention can also be used to catalyze the formation of peptide linkages with particular chiral moieties. In particular, the coupling of D amino acids in peptide synthesis protocols has proven problematic. The modified enzymes of this invention provide a convenient and efficient mechanism to preferentially couple a D- or an L-amino acid to an individual amino acid or to an amino acid present in a polypeptide.

Enzymatic peptide coupling is an attractive method for preparation of a variety of peptides because this method requires minimal protection of the substrate, proceeds under mild conditions, and does not cause racemization (Wong et al. (1994) pages 41-130 In: *Enzymes in Synthetic Organic Chemistry*, Pergamon Press, Oxford). As indicated above, the chemically modified mutant enzymes of this invention can incorporate D-amino acid esters as acyl donors in peptide synthesis or an α-branched amino acid amide as acyl acceptor in peptide synthesis to give a variety of dipeptides. These reaction are not possible with the wild-type enzymes.

Therefore the modified enzymes of the present invention can be used in organic synthesis to, for example, catalyze a desired reaction and/or to favor a certain stereoselectivity.

Of course the modified enzymes of this invention can also be utilized in more "traditional" applications. Thus, for example, the modified enzymes of this invention (e.g. in particular the proteases and/or lipases) can be formulated into known powdered and liquid detergents having a pH between 6.5 and 12.0 at levels of about 0.01 to about 5%, preferably about 0.1% to about 0.5%, by weight. These detergent cleaning compositions or additives can also include other enzymes such as known proteases, amylases, cellulases, lipases or endoglycosidases as well as builders and stabilizers.

In particularly preferred embodiments, the modified subtilisins are used in formulating various detergent compositions. A number of known compounds are suitable surfactants useful in such detergent compositions. These include non-ionic, anionic, cationic, anionic, or zwitterionic detergents (see, e.g., U.S. Pat. Nos. 4,404,128, and 4,261,868). A suitable detergent formulation is that described in example 7 of U.S. Pat. No. 5,204,015. The modified enzymes of this invention may provide improved wash performance in a detergent composition (as compared to previously known additives). Improves wash performance typically refers to increased cleaning of certain modified enzyme-sensitive stains such as grass or blood, as determined by a standard evaluation procedure (e.g. light reflectance) after a standard wash cycle.

The art is familiar with the different formulations that can be used as cleaning compositions. In addition to typical compositions, it is readily understood that the modified enzymes of the present invention may be used for any purpose that the native or wild-type enzymes are used. Thus, these modified enzymes can be used, for example, in bar or liquid soap applications, dish care formulations, contact lens cleaning solutions or products, peptide synthesis, feed applications such as feed additives or preparation of feed additives, waste treatment, textile application such as the treatment of fabrics, and as fusion-cleavage enzymes in protein production.

In another preferred embodiment, the modified enzymes of this invention are used in a method of treating a textile. The methods involve contacting a chemically modified mutant enzyme of this invention with a textile under conditions effective to produce a textile resistant to certain enzyme-sensitive stains (e.g. grass or blood stains). The method can be used to treat, for example, silk or wool. Enzyme treatments of such fabrics are know to those of skill in the art and are described for example in Research Disclosure 216,034, European Patent application No: 134,267, U.S. Pat. No. 4,533,359, and European Patent application 3244,259.

In still another embodiment, the modified enzymes of this invention are used in the preparation of an animal feed, for example, a cereal-based feed. The enzyme can be incorporated into essentially any cereal feed, e.g. a cereal comprising one or more of wheat, barley, maize, sorghum, rye, oats, triticale, and rice. Although the cereal component of a cereal-based feed constitutes a source of protein, it is usually necessary to include species of supplementary protein in the feed such as those derived form fish meal, meat, or vegetables. Sources of vegetable proteins include, but are not limited to soybeans, rape seeds, canola, soybean meal, rapeseed meal, and canola meal.

The inclusion of a modified enzyme in an animal feed can enable the crude protein value and/or the digestibility and/or the amino acid content of the feed to be increased. This permits a reduction in the amounts of alternative protein sources and/or amino acid supplements that are added to the feed.

The foregoing description of uses for the modified mutant enzymes of this invention is illustrative and not intended to create any special use limitation. One will appreciate that the uses of the enzymes of this invention are myriad and not to be confined to the uses enumerated herein.

V. Kits and Products Containing Chemically Modified Mutants.

In still another embodiment, this invention provides kits for synthesizing and/or screening modified mutants of this invention. Such kits preferably include one or more mutant serine hydrolases having one or more amino acid residues substituted with a cysteine as described herein. The kits may additionally include one or more methane sulfonate reagents as described herein that can be used to derivatize the mutant serine hydrolase. Such kits may additionally include one or more reagents and/or apparatus for performing such derivitizations.

In addition, the kits can include appropriate substrates and/or reactants for screening the chemically modified mutant enzyme for one or more desired activities as described herein.

In another embodiment this invention provides kits for the use of the modified mutant enzymes described herein. Such kits preferably contain one or more containers containing one or more of the chemically modified mutant serine hydrolases as described herein. Such kits can also include appropriate reagents and/or substrates to use the modified enzymes in one or more of the reactions described herein.

In addition, the kits may include instructional materials containing directions (i.e., protocols) for the practice of the syntheses, uses or assay methods described herein. Thus, for example, in one preferred embodiment, the instructional materials provide protocols derivatizing the mutant enzyme with one or more of the methane sulfonate reagents described herein. In another embodiment, the instructional materials may provide protocols describing the use of the modified enzyme in catalyzing formation of a peptide bond. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention. Throughout the Examples, amino acid positions are numbered by correspondence with positions in the amino acid sequence of *Bacillus amyloliquifaciens* subtilisin.

Example 1

Covalent Modification of Subtilisin *Bacillus lentus* Cysteine Mutants with Enantiomerically Pure Chiral Auxiliaries Causes Remarkable Changes in Activity Methanethiosulfonate reagents may be used to introduce virtually unlimited structural modifications in enzymes via reaction with the thiol group of cysteine. The covalent coupling of enantiomerically pure (R) and (S) chiral auxiliary methanethiosulfonate ligands to cysteine mutants of subtilisin *Bacillus lentus* induces spectacular changes in catalytic activity between diastereomeric enzymes. Amidase and esterase kinetic assays using a low substrate approximation were used to establish $k_{cat}/K_M$ values for the chemically modified mutants, and up to 3 fold differences in activity were found between diastereomeric enzymes. Changing the length of the carbon chain linking the phenyl or benzyl oxazolidinone ligand to the mutant N62C by a methylene unit reverses which diastereomeric enzyme is more active. Similarly, changing from a phenyl to benzyl oxazolidinone ligand at S166C reverses which diastereomeric enzyme is more active. Chiral modifications at S166C and L217C give CMMs having both high esterase $k_{cat}/K_M$'s and high esterase to amidase ratios with large differences between diastereomeric enzymes.

In this example, we illustrate changes in enzyme catalysis induced by the covalent attachment of enantiomerically pure MTS ligands derived from chiral auxiliaries to cysteine mutants of SBL (Scheme 1, FIG. 2). We selected mandelic acid and several oxazolidinones constructed from glycine, valine, phenylglycine, phenylalanine and cis-1-amino-indanol. We covalently linked the homochiral MTS ligands to cysteine mutants of SBL to create sets of diastereomeric chemically modified mutants (CMMs) allowing the observation of enzyme activity changes due solely to differences in the chiral environment at one site. This methodology acts as a very fine and precise probe of enzymatic catalysis, since any differences between diastereomeric enzymes are solely attributable to the spatial orientation of the ligand.

Enantiomerically pure MTS ligands, 1a-i, (FIG. 2) were synthesized and used to chemically modify the N62C, S156C, S166C and L217C mutants of SBL. These residues were targeted on the basis of SBL's x-ray crystal structure (X-ray structure solved by Rick Bott at Genencor International Inc. Brookhaven data base entry 1JEA of SBL). N62C is in the $S_2$ pocket near His-64 (nomenclature according to Schechter and Berger (1967) *Biochem. Biophys. Res. Commun.* 27: 157-162). S156C and S166C are at the bottom of the $S_1$ pocket. However, S156C is surface exposed and S166C is buried pointing into the pocket. L217C is found in $S_1'$ which is where the leaving group is bound. A kinetic assay of amidase and esterase activity was conducted on these new diastereomeric CMMs in order to investigate their properties and to probe any changes in selectivity.

Results

Synthesis of MTS Reagents 1a-i

Figure 3:
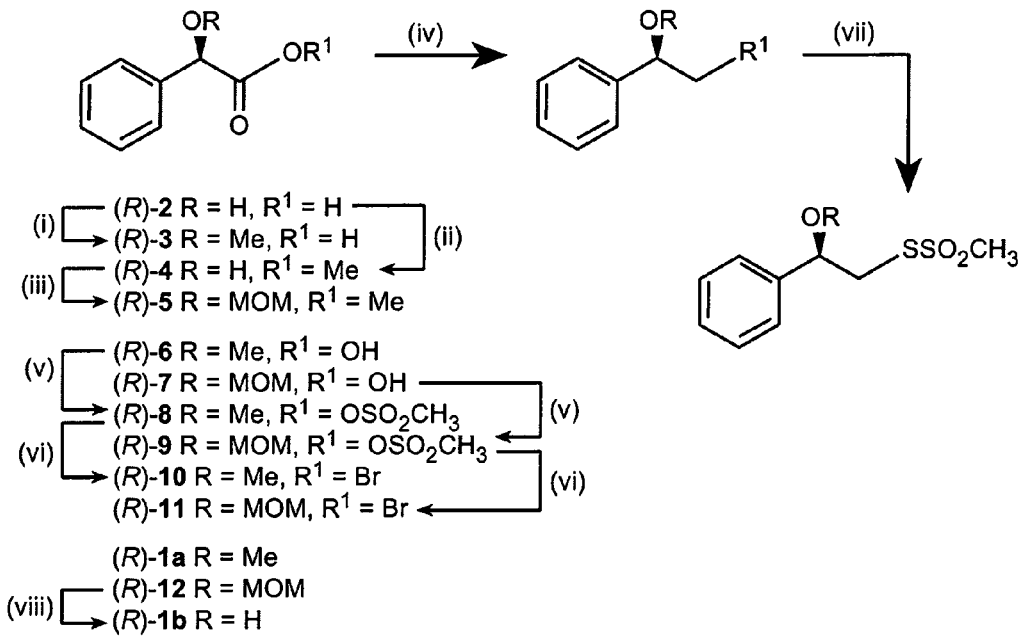
FIG. 3 illustrates synthesis scheme 2; the synthesis of mandelate-based ligands.

For the synthesis of the mandelate based MTS ligands, (R)-mandelic acid, (R)-2, was O-methylated with $Me_2SO_4$ (Reeve and Christoffel (1950) *J. Am. Chem. Soc.* 72: 1480-1483) in $NaOH/H_2O$ to give (R)-3 in 37% yield (Scheme 2). The acid, (R)-3, was reduced in 72% yield with borane in THF to alcohol, (R)-6, which was converted quantitatively to mesylate, (R)-8, in $CH_2Cl_2$. The mesylate was converted to bromide, (R)-10 (73%), by the action of LiBr in refluxing acetone, and methanethiosulfonate, (R)-1a, was formed in 84% yield from bromide, (R)-10, using $NaSSO_2CH_3$ in DMF. The methanethiosulfonate (S)-1a was made in an analogous fashion from (S)-mandelic acid (see Scheme 2, FIG. 3).

A similar approach allowed the synthesis of (R)-1b (Scheme 2). (R)-mandelic acid, (R)-2, was esterified to give (R)-4 which was protected as its methoxymethyloxy ether, (R)-5, in excellent yield (90% for 2 steps). The ester, (R)-5, was reduced with $LiBH_4$ to the alcohol, (R)-7 (98%), which was converted to the mesylate, (R)-9, and then to the bromide, (R)-11 (80% for 2 steps), using the same conditions as for the methyl ether analogue. This bromide was reacted with $NaSSO_2CH_3$ in DMF for 2 days to give (R)-12 in 61% yield. The alcohol was deprotected by the action of $TFA/H_2O$ to give the MTS reagent, (R)-1b, in 82% yield. The methanethiosulfonate (S)-1b was made in an analogous fashion from (S)-mandelic acid.

Figure 4:
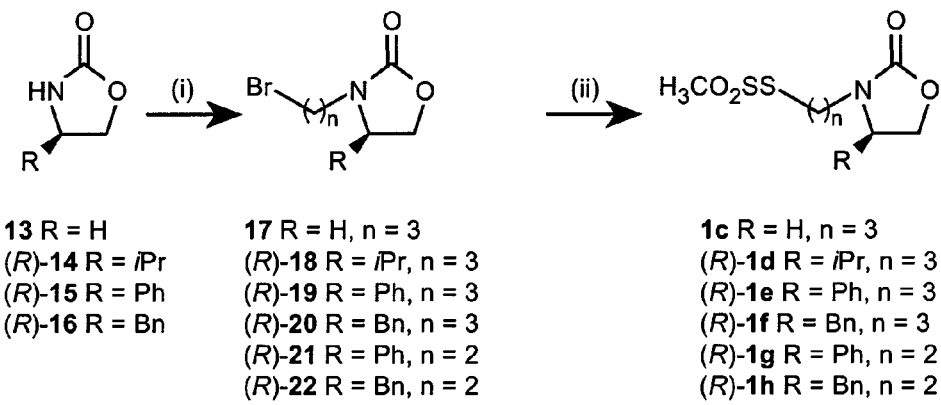
FIG. 4 illustrates synthesis scheme 3; the synthesis of oxazolidinone-based ligands.

The synthesis of oxazolidinone-based methanethiosulfonate ligands is shown in Scheme 3 (FIG. 4). Oxazolidinones have been widely used as chiral auxiliaries in asymmetric synthesis, and the degree of asymmetric induction can be excellent in chemical transformations ranging from alkylations to aldol reactions to Diels-Alder additions (Gage and Evans (1990) *Org. Synth.*, 68: 77-91; Ager et al. (1997) *Aldrichimica Acta*, 30: 3-12). The commercially available oxazolidinones, 13-(R)-16, were alkylated with 1,3-dibromopropane or 1,2-dibromoethane in DMSO/KOH (Isele and Luttringhaus (1971) *Synthesis*, 266-268) to give the bromides, 17-(R)-22, and converted to the methanethiosulfonates, 1c-(R)-1h, in 38-61% yield over 2 steps. The MTS reagents (S)-1d-(S)-1h were made in an identical manner from the (S) oxazolidinones.

Figure 5:
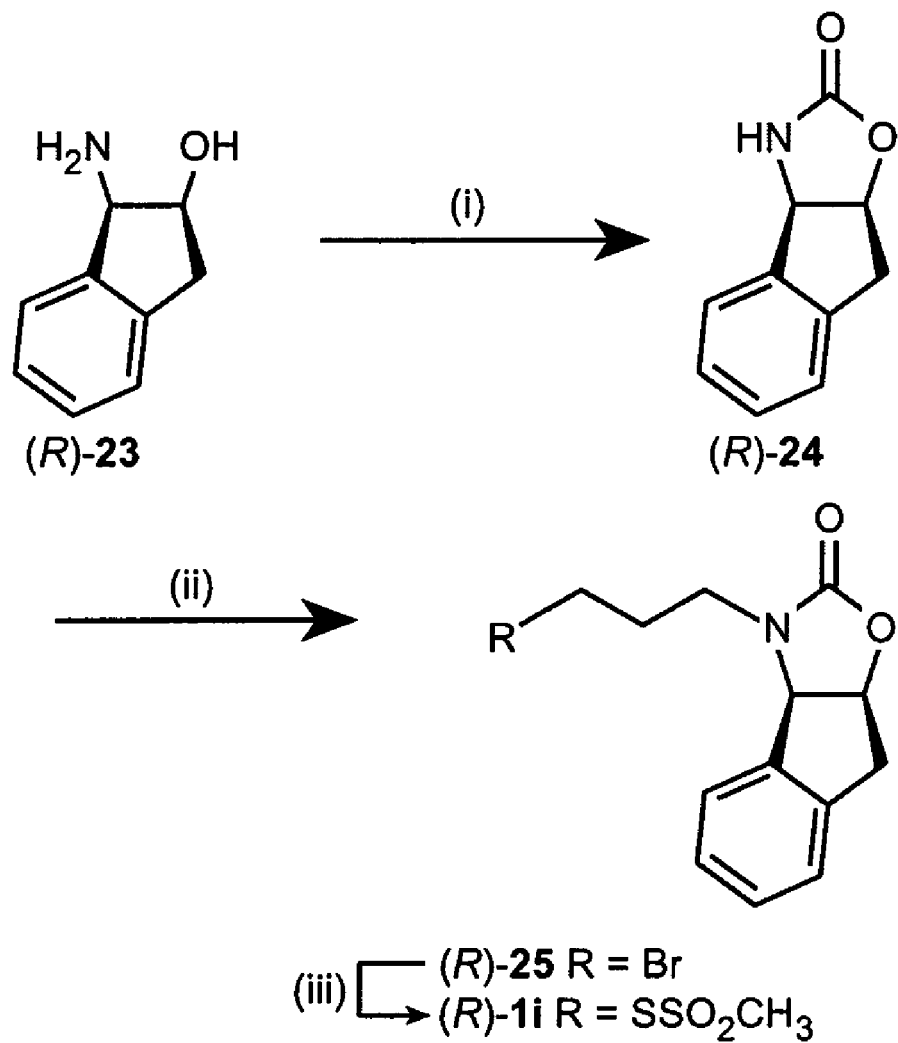
FIG. 5 illustrates synthesis scheme 4; the synthesis of indanol-based ligands.

The (1R,2S) oxazolidinone, (R)-24, of cis-1R-amino-2S-indanol, (R)-23, was prepared in quantitative yield by the reaction of (R)-23, triphosgene and Et$_3$N in CH$_2$Cl$_2$ (Scheme 4, FIG. 5) (Sibi et al. (1995) *Tetrahedron Lett.,* 36: 8961-8964). (R)-24 was then alkylated with 1,3-dibromopropane to make bromide, (R)-25, which was reacted with NaSSO$_2$CH$_3$ to give (R)-1i (49% yield for 2 steps). MTS reagent (S)-1i was synthesized from cis-1S-amino-2R-indanol in the same manner.

Enzyme Kinetic Assay

Subtilisin mutants, produced as described above, were modified with the homochiral MTS reagents. Characterization of the new CMMs was done by PMSF titration (Hsia et al. (1996) *Anal. Biochem.,* 242: 221-227) of their active sites, Ellman's titration (Ellman et al. (1961) *Biochem. Pharmacol.,* 7: 88-95) of residual thiol (≦2% in all cases), ES-MS after FPLC purification (mol. wt. ±6 mass units in all cases), and by nondenaturing gradients gels which all showed one band.

Amidase and esterase kinetic assays were conducted on these new diastereomeric CMMs. Both assays were run using a low substrate concentration in order to obtain a specificity constant ($k_{cat}/K_M$) that gave us an idea of the performance of the CMMs and allowed us to compare diastereomeric enzymes. (At low substrate concentration, ($k_{cat}/K_M$)=$v_{initial}$/[Enzyme][Substrate]). The results are presented in Table 1.

TABLE 1

Kinetic Assay[a] of SBL CMMs.

| enzyme | amidase assay $k_{cat}/K_M$ (mM$^{-1}$ s$^{-1}$) (R) | (S) | esterase assay $k_{cat}/K_M$ (mM$^{-1}$ s$^{-1}$) (R) | (S) |
|---|---|---|---|---|
| WT[b] | 209 ± 15 | | 3560 ± 540 | |
| N62C[b] | 92 ± 7 | | 4380 ± 655 | |
| N62C-a | 218 ± 9 | 226 ± 11 | 5156 ± 131 | 5483 ± 106 |
| N62C-b | 187 ± 10 | 220 ± 9 | 3571 ± 73 | 3054 ± 171 |
| N62C-c | 181 ± 6 | | 9185 ± 407 | |
| N62C-d | 333 ± 13 | 284 ± 5 | 5440 ± 78 | 4098 ± 151 |
| N62C-e | 458 ± 13 | 308 ± 7 | 13868 ± 920 | 6564 ± 157 |
| N62C-f | 245 ± 3 | 150 ± 1 | 4995 ± 87 | 3261 ± 163 |
| N62C-g | 185 ± 4 | 244 ± 7 | 3635 ± 58 | 4120 ± 159 |
| N62C-h | 262 ± 5 | 335 ± 7 | 6149 ± 202 | 7591 ± 209 |
| N62C-i | 165 ± 3 | 228 ± 6 | 4675 ± 143 | 3279 ± 135 |
| S166C[b] | 84 ± 4 | | 350 ± 41 | |
| S166C-a | 72 ± 2 | 26 ± 1 | 1677 ± 16 | 1246 ± 48 |
| S166C-b | 48 ± 2 | 15 ± 1 | 1061 ± 18 | 929 ± 27 |
| S166C-c | 75 ± 1 | | 4898 ± 196 | |
| S166C-d | 75 ± 1 | 76 ± 1 | 4215 ± 157 | 4475 ± 196 |
| S166C-e | 101 ± 3 | 64 ± 2 | 4076 ± 111 | 3964 ± 90 |
| S166C-f | 22 ± 1 | 52 ± 1 | 1495 ± 134 | 3277 ± 134 |
| S166C-g | 104 ± 2 | 37 ± 1 | 4281 ± 96 | 4069 ± 165 |
| S166C-h | 35 ± 1 | 80 ± 2 | 2150 ± 107 | 5446 ± 211 |
| S166C-i | 20 ± 1 | 47 ± 1 | 1488 ± 54 | 4556 ± 170 |
| L217C[b] | 51 ± 4 | | 5540 ± 798 | |
| L217C-a | 204 ± 5 | 144 ± 4 | 10140 ± 231 | 8075 ± 144 |
| L217C-b | 175 ± 3 | 227 ± 6 | 9147 ± 167 | 8714 ± 324 |
| L217C-c | 85 ± 1 | | 5917 ± 200 | |
| L217C-d | 105 ± 3 | 104 ± 2 | 8315 ± 171 | 9296 ± 665 |
| L217C-e | 120 ± 4 | 184 ± 3 | 8015 ± 413 | 6696 ± 255 |
| L217C-f | 73 ± 2 | 79 ± 2 | 6435 ± 169 | 5128 ± 163 |
| L217C-i | 118 ± 4 | 171 ± 7 | 7914 ± 272 | 7321 ± 330 |
| S156C[b] | 147 ± 8 | | —[c] | |
| S156C-a | 102 ± 2 | 98 ± 1 | 2468 ± 45 | 1928 ± 59 |
| S156C-b | 85 ± 3 | 90 ± 2 | 2284 ± 81 | 2528 ± 68 |
| S156C-e | 88 ± 2 | 92 ± 4 | 1796 ± 63 | 2179 ± 38 |

[a]The amidase assay was done at 0.05 and 0.1 mM N-Suc-AAPF-pNA in 0.1 M Tris at pH 8.6, and the esterase assay was conducted at 0.015 and 0.03 mM N-Suc-AAPF-SBn in 0.1 M Tris at pH 8.6. Assay errors are the mean standard errors from sets of six replicates.
[b]$k_{cat}/K_M$ obtained by full kinetic run of 8 substrate concentrations and calculation of independent $k_{cat}$ and $K_M$ values. Errors were obtained from the curve-fitting errors in $k_{cat}$ and $K_M$.
[c]Determination of esterase $k_{cat}/K_M$ for S156C was impossible due to rapid reaction between the mutant and Ellman's reagent.

Discussion

Figure 6A:
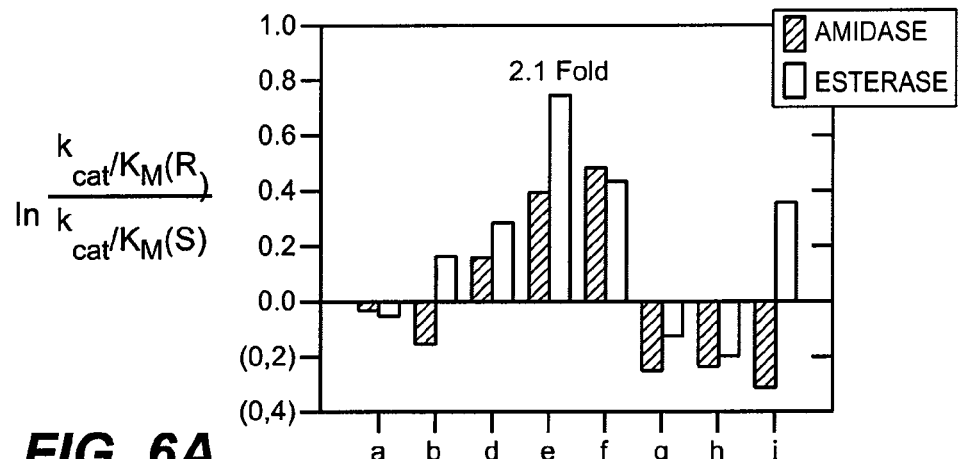
FIG. 6A illustrates a comparison of N62C CMM specificity constants, wherein these positions are numbered by correspondence with positions in the amino acid sequence of *Bacillus amyloliquefaciens* subtilisin.
Figure 6B:
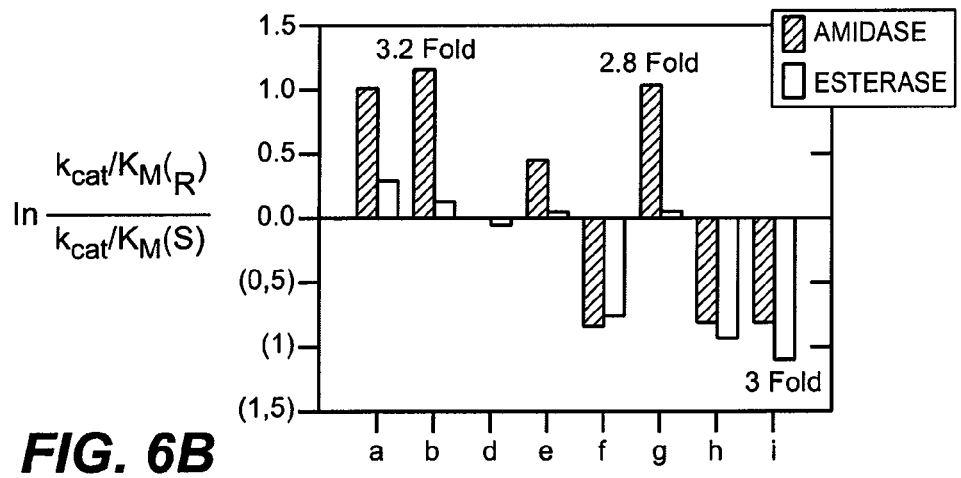
FIG. 6B illustrates a comparison of S166C CMM specificity constants, wherein these positions are numbered by correspondence with positions in the amino acid sequence of *Bacillus amyloliquefaciens* subtilisin.
Figure 6C:
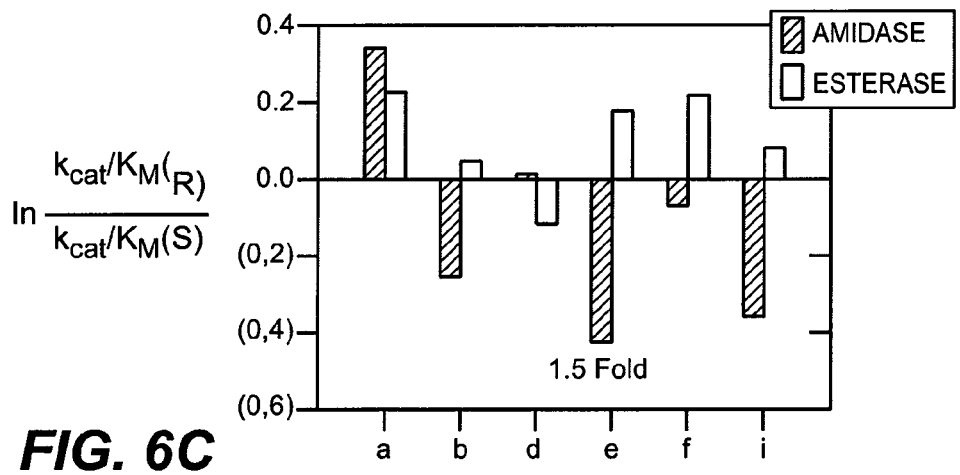
FIG. 6C illustrates a comparison of L217C CMM specificity constants, wherein these positions are numbered by correspondence with positions in the amino acid sequence of *Bacillus amyloliquefaciens* subtilisin.

Chiral auxiliaries are employed in asymmetric organic synthesis to block one diastereotopic face of a molecule thus forcing the reaction to the other face which results in the formation of solely one diastereomer. The covalent coupling of enantiomerically pure (R) and (S) chiral auxiliary MTS ligands to SBL cysteine mutants has caused remarkable changes in enzyme activity. We can attribute these changes uniquely to the difference in spatial orientation at the ligand stereocenter when comparing diastereomeric enzymes. The extraordinary differences in catalytic activity between diastereomeric enzymes can be compared in FIGS. 6A, 6B, and 6C.

N62C

Of the N62C CMMs, the N62C-e set of diastereomeric CMMs is remarkable for displaying both high catalytic activity and a large difference between diastereomers. N62C—(R)-e is both an excellent amidase (2.2 fold better than WT) and an excellent esterase (3.9 fold better than WT). In addition, the (S)-diastereomer is a good amidase (308 mM$^{-1}$ s$^{-1}$) and esterase (6564 mM$^{-1}$ s$^{-1}$), but not as good as the (R)-diastereomer. Thus, there is a large difference between the two diastereomeric CMMs with respect to esterase performance ((R) is 2.1 fold better than (S)) and a moderate difference in amidase activity. At the same time, the achiral modified mutant (N62C-c) is only as good an amidase (181 mM$^{-1}$ s$^{-1}$) as WT and a poorer esterase (9185 mM$^{-1}$ s$^{-1}$) than N62C—(R)-e. These observations indicate that not only does the addition of a phenyl group at the 4 position of the oxazolidinone ring increase enzyme activity, but that the addition must be (R)-phenyl. Thus, the (R)-e modification at N62C is affecting the enzyme in a unique manner. Individual $k_{cat}$ and $K_M$ values were determined for the three enzymes, N62C-c and the N62C-e set, and these results are presented in Table 2 along with WT values for comparison. It is obvious that the kinetic assay using the low substrate approximation slightly underestimates the $k_{cat}/K_M$ values, but the ratios of catalytic activity between diastereomeric enzymes remains approximately the same.

TABLE 2

Kinetic Parameters of WT and selected SBL CMMs[a]

| Enzyme | amidase | | | | esterase | | | |
|---|---|---|---|---|---|---|---|---|
| | $k_{cat}$ (s$^{-1}$) | $K_M$ (mM) | $k_{cat}/K_M$ (mM$^{-1}$ s$^{-1}$) | $k_{cat}/K_M$ (mM$^{-1}$ s$^{-1}$) assay | $k_{cat}$ (s$^{-1}$) | $K_M$ (mM) | $k_{cat}/K_M$ (mM$^{-1}$ s$^{-1}$) | $k_{cat}/K_M$ (mM$^{-1}$ s$^{-1}$) assay |
| WT | 153 ± 4 | 0.73 ± 0.05 | 209 ± 15 | — | 1940 ± 180 | 0.54 ± 0.07 | 3560 ± 540 | — |
| N62C—(R)-e | 163 ± 2 | 0.26 ± 0.01 | 627 ± 26 | 458 ± 13 | 2894 ± 117 | 0.15 ± 0.02 | 19293 ± 2895 | 13868 ± 920 |

TABLE 2-continued

Kinetic Parameters of WT and selected SBL CMMs[a]

| | amidase | | | | esterase | | | |
|---|---|---|---|---|---|---|---|---|
| Enzyme | $k_{cat}$ (s$^{-1}$) | $K_M$ (mM) | $k_{cat}/K_M$ (mM$^{-1}$ s$^{-1}$) | $k_{cat}/K_M$ (mM$^{-1}$ s$^{-1}$) assay | $k_{cat}$ (s$^{-1}$) | $K_M$ (mM) | $k_{cat}/K_M$ (mM$^{-1}$ s$^{-1}$) | $k_{cat}/K_M$ (mM$^{-1}$ s$^{-1}$) assay |
| N62C—(S)-e | 164 ± 2 | 0.41 ± 0.02 | 400 ± 20 | 308 ± 7 | 1106 ± 45 | 0.15 ± 0.02 | 7373 ± 1098 | 6564 ± 157 |
| N62C-c | 193 ± 3 | 0.63 ± 0.03 | 307 ± 16 | 181 ± 6 | 3447 ± 66 | 0.26 ± 0.01 | 13258 ± 710 | 9185 ± 407 |

[a]Notation as in Table 1.

Modification of N62C with (R)-1e, (S)-1e and 1c decreases $K_M$ indicating better binding of the substrate, and in the case of amidase activity, it is this $K_M$ effect that is the source of the increased $k_{cat}/K_M$, since these N62C CMMs have similar $k_{cat}$ values to the WT. However, the changes in esterase activity for these enzymes are more complex. N62C—(R)-e and N62C-c show significantly higher $k_{cat}$ and lower $K_M$ values than WT giving overall 5.4 fold and 3.7 fold respectively better esterase activity than WT. The N62C—(S)-e CMM does not display these characteristics. While it does bind the substrate very well and achieve half its maximum turnover rate at low substrate concentration ($K_M$=0.15 mM), its $k_{cat}$ (1106 s$^{-1}$) is much lower than WT. Therefore, it appears that a 4R-phenyl substitution on the oxazolidinone improves overall catalytic performance by increasing $k_{cat}$ and lowering $K_M$.

In an attempt to improve on these results, the ethyl linked phenyl and benzyl oxazolidinone N62C CMMs were prepared (N62C-g and N62C-h). Surprisingly, there was a reversal of which modification made the best enzyme. In the case of the propyl linked CMMs (N62C-e and N62C-f), the (R) modification was the best amidase and esterase for both phenyl and benzyl groups. However, the (S) modification was the best when these same groups were ethyl linked. This brings to mind the flipping of substrate preference for transesterification reactions catalyzed by WT from (S) to (R) and back to (S) for secondary alcohols, β-branched primary alcohols and γ-branched primary alcohols respectively (Lloyd et al. (1998) *Tetrahedron: Asymmetry*, 9: 551-561). However, in the present situation, the substrate does not change. Rather, the ability of the enzyme to convert substrate to product is altered depending upon the stereocentre of the covalently linked ligand as well as the number of bonds present in the link between the enzyme backbone and the stereocentre.

S166C

Modifications at S166C produced many sets of diastereomeric CMMs with large differences in activity. Primarily, the 1a, 1b, 1f, 1g, 1 h and 1i modifications produced CMMs with greater then 2 fold variances between diastereomeric CMMs. The largest difference of any set of CMMs was achieved with S166C-b which has a $[k_{cat}/K_M(R)]/[k_{cat}/K_M(S)]$ ratio of 3.2. Notably, the modifications with the phenyl and benzyl oxazolidinones at S166C reverse which diastereomeric CMM has greater catalytic activity in a way similar to the same modifications at N62C. However, at S166C the reversal is caused by the addition of a methylene unit directly to the stereocentre of the oxazolidinone ligand. The (R)-phenyl oxazolidinone modifications ((R)-e and (R)-g) produce S166C CMMs that are better than the (S) analogs, but the (S)-benzyl oxazolidinones ((S)-f and (S)-h) give significantly better S166C CMMs than the (R).

Figure 7A:
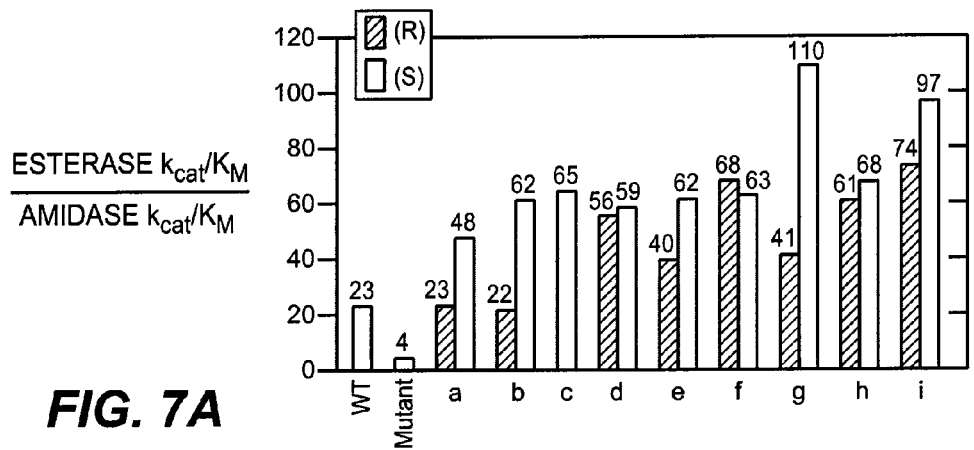
FIG. 7A illustrates the changes in esterase to amidase activity ratios in S166C CMMs, wherein these positions are numbered by correspondence with positions in the amino acid sequence of *Bacillus amyloliquefaciens* subtilisin.

Though none of these CMMs showed significantly greater than WT activity, S166C—(S)-g and S166C—(S)-i are good esterases (4069 mM$^{-1}$ s$^{-1}$ and 4556 mM$^{-1}$ s$^{-1}$ respectively) and have high esterase/amidase ratios of 110 and 97 making them good candidates as peptide ligation catalysts (FIG. 7A). S166C—(S)-a and S166C—(S)-b have relatively high esterase/amidase ratios (48 and 62) compared to S166C (4) and WT, but these two CMMs are very poor esterases. Interestingly, for chiral modifications at S166C, the (S)-ligand consistently gives a CMM with a higher esterase to amidase ratio than the (R)-ligand, except in the case of the if where the two diastereomeric enzymes have similar ratios.

L217C

Figure 7B:
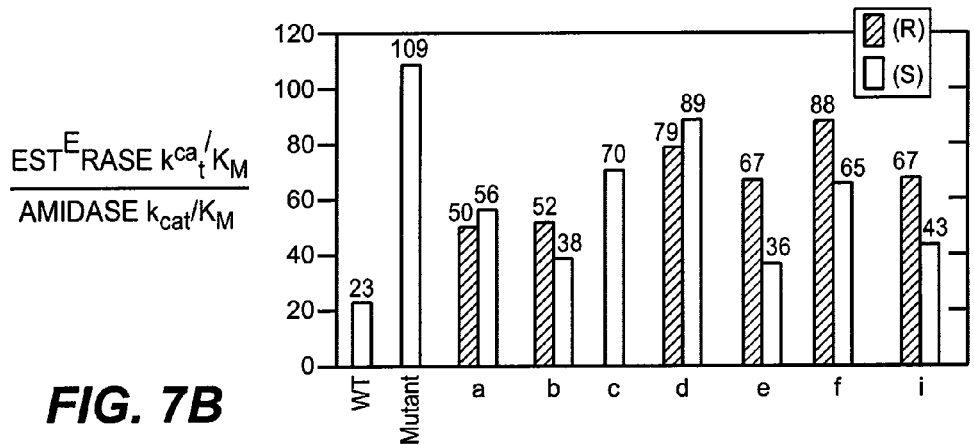
FIG. 7B illustrates the changes in esterase to amidase activity ratios in L217C CMMs, wherein these positions are numbered by correspondence with positions in the amino acid sequence of *Bacillus amyloliquefaciens* subtilisin.

The chiral modifications at L217C produced many CMMs that could be used as peptide ligation catalysts due to their high esterase/amidase ratio (FIG. 7B). L217C—(S)-d has a very high esterase $k_{cat}/K_M$ (9296 mM$^{-1}$ s$^{-1}$) and a low amidase value (104 mM$^{-1}$ s$^{-1}$) giving it a relatively high esterase/amidase ratio of 89. L217C—(R)-f has a similar ratio of 88 and a good esterase $k_{cat}/K_M$ (6435 mM$^{-1}$ s$^{-1}$). While it is true that the L217C has the highest ratio in the group (109), this is mitigated by its lower esterase $k_{cat}/K_M$ (5540 mM$^{-1}$ s$^{-1}$). Therefore, these CMMs should catalyze very efficiently the formation of peptide bonds from an ester acyl donor and amine nucleophile. No large differences were observed between diastereomeric CMMs.

S156C

Modification of S156C by 1a, 1b and 1e revealed no enzymes with either high activity or large difference between diastereomers. This is not surprising, because the S156C side chain is surface exposed, so it is probable that the ligand modifier points out of the pocket or is not closely associated with the pocket. For this reason, the kinds of subtle variations expected due to spatial orientation were not found at S156C. As a result, no further modifications were made of this mutant.

Conclusion

It has been found that the modification of cysteine mutants of SBL with enantiomerically pure MTS ligands effects considerable changes in enzyme activity. Amidase and esterase kinetic assays using a low substrate approximation, found up to 3 fold differences in activity between diastereomeric enzymes. N62C—(R)-e was particularly remarkable. Its amidase $k_{cat}/K_M$ was 1.56 fold better than its diastereomer, N62C—(S)-e, and 3 fold better than WT. Also, the esterase $k_{cat}/K_M$ of N62C—(R)-e was 2.6 fold better than its diastereomer and 5.4 fold better than WT. Changing the length of the carbon chain linking the phenyl or benzyl oxazolidinone ligand to N62C by a methylene unit reverses which diastereomeric enzyme is more active. In a similar fashion, changing from a phenyl to benzyl oxazolidinone ligand at S166C reverses which diastereomeric enzyme is more active. Work is in progress investigating the peptide ligation and transesterification capabilities of the CMMs discussed in this paper.

In addition, the attachment of enantiomerically pure ligands containing charged groups to SBL mutants is being pursued.

Experimental

The N62C, L217C, S166C, and S156C mutants of subtilisin *Bacillus lentus* were prepared and purified by the general method (Stabile et al. (1996) *Bioorg. Med. Chem. Lett.* 6: 2501-2506). Spectrophotometric measurements were made on a Perkin-Elmer Lamda 2 spectrophotometer.

Melting Points were determined using an Electrothermal IA9000 series Digital Melting Point Apparatus, and are uncorrected. Optical Rotation data were obtained using a Perkin Elmer 243B polarimeter. Compounds were identified by their $^1$H (200 MHz) and $^{13}$C (50.3 MHz) NMR spectra, run using a Varian Gemini NMR spectrometer, and HRMS data were acquired using a Micromass 70-250S (double focussing) mass spectrometer for EI spectra and a Micromass ZAB-SE for FAB spectra. Enantiomeric excesses of methanethiosulfonates ((R)-1a, (S)-1a, (R)-1b and (S)-1b) were determined by HPLC on a Chiralcel OJ column using a hexane:isopropanol eluent system. Enantiomeric excesses (ee) of bromides ((R)-18, (S)-18, (R)-19, (S)-19, (R)-20, (S)-20, (R)-21, (S)-21, (R)-22, (S)-22, (R)-25 and (S)-25) were determined by HPLC on a Chiralcel OD column using the same eluent system.

Preparation of Methanethiosulfonate Reagents (R)-2-methoxy-2-phenyl-ethylmethanethiosulfonate
((R)-1a)

(R)-mandelic acid (4.678 g, 30.75 mmol) was dissolved in 6M NaOH (50 mL, 300 mmol) and dimethyl sulfate (14.6 mL, 154 mmol) was added over 1 hr so that the temperature stayed at 50° C. After another hr of stirring, H$_2$O (50 mL) was added, and the solution was acidified to pH 1 with 12M HCl. The mixture was saturated with NaCl, extracted with EtOAc (3×100 mL), and the extracts dried with Na$_2$SO$_4$. After filtration and evaporation under reduced pressure, the solid was pulverized, refluxed in hexanes (100 mL) for 15 min and hot filtered. The insoluble (R)-mandelic acid (2.71 g, 58%) was recovered, and the hexanes evaporated under reduced pressure to give (R)-2-methoxy-mandelic acid, (R)-3 (1.91 g, 37%) which was used directly in the next step.

(R)-3 (1.91 g, 11.46 mmol), was placed under Ar and dry THF (15 mL) was added. The resulting solution was cooled to 0° C. and 1M BH$_3$.THF (17.2 mL, 17.2 mmol) was added over 1 min. The ice bath was removed, and the reaction was allowed to warm to 20° C. After stirring overnight, the reaction mixture was poured into a stirred mixture of EtOAc (200 mL)/saturated aqueous NaHCO$_3$ (100 mL). The aqueous layer was saturated with NaCl and extracted with EtOAc (3×150 mL). The combined EtOAc fractions were dried with MgSO$_4$, filtered and evaporated under reduced pressure. Flash Chromatography was conducted using a step gradient (25% EtOAc/75% hexanes to 33% EtOAc/67% hexanes) to give (R)-2-methoxy-2-phenyl-1-ethanol, (R)-6 (1.26 g, 72%), as a colorless oil. [α]$^{25}_D$=−114.6 (c 1.27, EtOH) [Aller et al. (1995) *J. Org. Chem.*, 60: 4449-4460, [α]$^{25}_D$=−117.3 (c 1.006, EtOH)]; IR, $^1$H NMR and $^{13}$C NMR data were identical to the literature (Barrett and Rys (1995) *Chem. Soc. Perkin Trans.* 1: 1009-1017).

(R)-6 (1.25 g, 8.213 mmol) and Et$_3$N (2.29 mL, 16.43 mmol) were dissolved in CH$_2$Cl$_2$ (20 mL) under Ar and cooled to 0° C. MsCl (0.95 mL, 12.27 mmol) was added over 1 min, and stirred for 10 min. The ice bath was removed, and the solution was stirred overnight. The reaction was poured into EtOAc (200 mL)/saturated aqueous NaHCO$_3$ (100 mL), stirred and saturated with NaCl. The aqueous layer was extracted with EtOAc (3×150 mL), and the combined organic fractions were dried with MgSO$_4$. After filtration and evaporation under reduced pressure, the crude product was purified by flash chromatography using 50% EtOAc/50% hexanes to give (R)-2-methoxy-2-phenyl-1-ethylmethanesulfonate, (R)-8, quantitatively (1.88 g) as a colorless oil. [α]$^{25}_D$=−97.4 (c 1.36, CHCl$_3$); $^1$H NMR (CDCl$_3$) δ 7.30-7.40 (5H, m), 4.47-4.52 (1H, m), 4.20-4.36 (2H, m), 3.30 (3H, s), 2.99 (3H, s); $^{13}$C NMR (CDCl$_3$) δ 136.6, 128.8, 126.9, 81.5, 72.7, 57.0, 37.6.

(R)-8 (1.88 g, 8.160 mmol) and LiBr (3.54 g, 40.76 mmol) were refluxed in freshly distilled acetone (20 mL) for 20 hr under a CaCl$_2$ drying tube. After cooling and evaporation to dryness under reduced pressure, hexanes (30 mL) were added and the mixture filtered. The filtrate was evaporated under reduced pressure, and flash chromatography of the crude product was done using a step gradient (hexanes to 5% EtOAc/95% hexanes) to give (R)-2-methoxy-2-phenyl-1-ethyl bromide, (R)-10, (1.284 g, 73%), as a colorless oil. [α]$^{25}_D$=−71.6 (c 1.26, MeOH) [Casey et al. (1969) *Am. Chem. Soc.*, 91: 2789-2790 for the (S) enantiomer [α]$^{25}_D$=+73 (MeOH)]; $^1$H NMR (CDCl$_3$) δ 7.31-7.40 (5H, m), 4.36-4.42 (1H, m), 3.45-3.60 (2H, m), 3.32 (3H, s); $^{13}$C NMR (CDCl$_3$) δ 139.0, 128.6, 128.5, 126.7, 83.4, 57.2, 36.2; HRMS (EI) m/z: calcd for C$_9$H$_{11}$OBr, 213.9993; found, 213.9988.

(R)-10 (1.28 g, 5.951 mmol) and sodium methanethiosulfonate (1.04 g, 7.752 mmol) were dissolved in dry DMF (10 mL) under Ar and heated to 70° C. After stirring for 24 hr, the DMF was evaporated under reduced pressure. The crude product was dissolved in EtOAc, filtered, and the filtrate was evaporated under reduced pressure. flash chromatography using a step gradient (5% EtOAc/95% hexanes to 33% EtOAc/67% hexanes) gave the tile compound, (R)-1a (1.235 g, 84%, ee≧98%), as a colorless oil. [α]$^{25}_D$=−90.4 (c 0.94, CHCl$_3$); $^1$H NMR (CDCl$_3$) δ 7.31-7.39 (5H, m), 4.42-4.48 (1H, m), 3.41-3.46 (2H, m), 3.27 (3H, s), 3.24 (3H, s); $^{13}$C NMR (CDCl$_3$) δ 139.0, 128.7, 128.5, 126.6, 82.3, 56.9, 50.3, 43.4; HRMS (FAB+) m/z: calcd for C$_{10}$H$_{14}$O$_3$S$_2$+H, 247.0463; found, 247.0470.

(S)-2-methoxy-2-phenyl-ethylmethanethiosulfonate
((S)-1a)

(S)-3 was prepared in the same manner as the (R)-3. From (S)-mandelic acid (4.00 g, 26.29 mmol) was obtained (S)-1 (1.301 g, 30%).

(S)-6 was prepared in the same manner as the (R)-6. From (S)-3 (1.20 g, 7.221 mmol) was obtained (S)-6 (0.903 g, 82%). Its IR, $^1$H NMR and $^{13}$C NMR data were identical to (R)-6. [α]$^{25}_D$=+115.0 (c 1.26, EtOH).

(S)-8 was prepared in the same manner as the (R)-8. From (S)-6 (0.883 g, 5.802 mmol) was obtained (S)-8 (1.33 g, 100%). Its $^1$H NMR and $^{13}$C NMR data were identical to (R)-8. [α]$^{25}_D$=+95.0 (c 1.70, CHCl$_3$).

(S)-10 was prepared in the same manner as (R)-10. From (S)-8 (1.33 g, 5.773 mmol) was obtained (S)-10 (1.02 g, 81%). Its $^1$H NMR and $^{13}$C NMR data were identical to (R)-10. [α]$^{25}_D$=+72.4 (c 1.15, MeOH).

(S)-1a was prepared in the same manner as (R)-1a. From (S)-10 (1.00 g, 4.649 mmol) was obtained (S)-1a (0.961 g, 84%, ee≧98%). Its $^1$H NMR and $^{13}$C NMR data were identical to (R)-1a. [α]$^{25}_D$=+93.8 (c 1.002, CHCl$_3$); HRMS (FAB+) m/z: calcd for C$_{10}$H$_{14}$O$_3$S$_2$+H, 247.0463; found, 247.0474.

(R)-2-hydroxy-2-phenyl-ethylmethanethiosulfonate ((R)-1b)

(R)-Mandelic acid (2.568 g, 16.87 mmol) and 2,2-dimethoxypropane (5.1 mL, 41.48 mmol) were dissolved in MeOH (100 mL) and 12M HCl (100 mL) was added. The resulting solution was stirred for 20 hr under a CaCl$_2$ tube and evaporated to dryness under reduced pressure. EtOAc (100 mL) and saturated aqueous NaHCO$_3$ (100 mL) were added, and the aqueous phase was extracted with EtOAc (3×100 mL). The organic fractions were dried with MgSO$_4$, and evaporated under reduced pressure to give (R)-methyl mandelate, (R)-4, quantitatively (2.78 g) as a white solid which was of sufficient purity for the next step.

(R)-4 (1.695 g, 10.20 mmol) and Hunig's base (6.22 mL, 35.70 mmol) were dissolved in dry CH$_2$Cl$_2$ (25 mL) at 0° C. under Ar. MOM-Cl (2.32 mL, 30.55 mmol) was dripped into the solution over 1 min, and the reaction was stirred at 20° C. for 16 hr. The solution was poured into a mixture of EtOAc (200 mL)/ice/3M HCl (100 mL) and stirred for 5 min. The aqueous layer was extracted with EtOAc (3×150 mL), and the combined organic fractions were dried with MgSO$_4$. Flash Chromatography was performed using a step gradient (10% EtOAc/90% hexanes to 25% EtOAc/75% hexanes) to give (R)-2-methyloxymethoxy methyl mandelate, (R)-5 (1.935 g, 90%), as a colorless oil. $[\alpha]^{25}_D$=−133.5 (c 1.41, CHCl$_3$); [Barrett and Rys (1995) *Chem. Soc. Perkin Trans.* 1: 1009-1017, for the (S) enantiomer $[\alpha]^{25}_D$=+5.9 (c 1.11, CHCl$_3$); IR, $^1$H NMR and $^{13}$C NMR data were identical to the literature (Barrett and Rys, Chem. (1995) *Soc. Perkin Trans.* 1:, 1009-1017).

(R)-5 (1.924 g, 9.152 mmol) was dissolved in dry THF (50 mL) at 0° C. under Ar, and LiBH$_4$ (0.498 g, 22.87 mmol) was added. The reaction was stirred for 16 hr at 20° C., and then poured into a stirred mixture of EtOAc (200 mL)/saturated aqueous NaHCO$_3$ (150 mL). After the reaction had subsided, the aqueous layer was extracted with EtOAc (3×200 mL), and the combined organic fractions were dried with MgSO$_4$. The crude product was purified by flash chromatography using a step gradient (25% EtOAc/75% hexanes to 33% EtOAc/67% hexanes) to give (R)-2-methyloxymethoxy-2-phenyl-1-ethanol, (R)-7 (1.63 g, 98%), as a colorless oil. $[\alpha]^{25}_D$=−189.9 (c 1.72, CHCl$_3$); [ Ko and Eliel (1986) *J. Org. Chem.*, 51: 5353-5362 for the (S) enantiomer $[\alpha]^{20}_D$=+196 (c 2.67, CHCl$_3$)]; IR, $^1$H NMR and $^{13}$C NMR data were identical to the literature (Ko and Eliel (1986) *J. Org. Chem.*, 51, 5353-5362).

(R)-2-methyloxymethoxy-2-phenyl-1-ethylmethanesulfonate, (R)-9, was prepared in the same manner as (R)-8. (R)-7 (1.530 g, 8.396 mmol) was converted quantitatively to (R)-9 (2.175 g). $[\alpha]^{25}_D$=−141.6 (c 1.10, CHCl$_3$); $^1$H NMR (CDCl$_3$) δ 7.35 (5H, s), 4.89-4.95 (1H, m), 4.56-4.65 (2H, AB q), 4.25-4.40 (2H, m), 3.36 (3H, s), 2.95 (3H, s); $^{13}$C NMR (CDCl$_3$) δ 136.6, 128.7, 127.1, 94.4, 75.5, 72.3, 55.6, 37.4.

(R)-2-methyloxymethoxy-2-phenyl-1-ethyl bromide, (R)-11, was prepared in the same manner as (R)-10. (R)-9 (2.035 g, 7.817 mmol) was converted to (R)-11 (1.536 g, 80%). $[\alpha]^{25}_D$=−130.9 (c 1.29, MeOH); $^1$H NMR (CDCl$_3$) δ 7.35 (5H, s), 4.82-4.88 (1H, m), 4.57-4.66 (2H, AB q), 3.49-3.65 (2H, m), 3.43 (3H, s); $^{13}$C NMR (CDCl$_3$) δ 139.0, 128.6, 128.5, 126.9, 94.5, 77.7, 55.8, 36.2; HRMS (EI) m/z: calcd for C$_{10}$H$_{13}$O$_2$Br, 244.0099; found, 244.0091.

(R)-2-methyloxymethoxy-2-phenyl-1-ethylmethanethiosulfonate, (R)-12, was prepared in the same manner as (R)-1a. (R)-10 (1.458 g, 5.948 mmol) was converted to (R)-12 (1.005 g, 61%). $[\alpha]^{25}_D$=−149.6 (c 2.23, CHCl$_3$); $^1$H NMR (CDCl$_3$) δ 7.36 (5H, s), 4.88-4.94 (1H, m), 4.56 (2H, s), 3.48-3.51 (2H, m), 3.40 (3H, s), 3.23 (3H, s); $^{13}$C NMR (CDCl$_3$) δ 139.0, 128.7, 128.6, 126.9, 94.3, 76.3, 55.9, 50.5, 43.4; HRMS (FAB+) m/z: calcd for C$_{11}$H$_{16}$O$_4$S$_2$+H, 277.0569; found, 277.0600.

(R)-12 (0.864 g, 3.126 mmol) was suspended in H$_2$O (10 mL) and trifluoroacetic acid (10 mL) was added at 0° C. The solution was stirred at 20° C. for 40 hr, and the volatiles were evaporated under reduced pressure to near dryness. H$_2$O (20 mL) was added, and the suspension was evaporated to dryness. Finally, toluene (50 mL) was added, and the solution was evaporated to dryness. The crude product was purified by flash chromatography using a step gradient (25% EtOAc/75% hexanes to 33% EtOAc/67% hexanes) to give the title compound, (R)-1b (0.689 g, 95%, ee≧98%), as white crystals. An analytical sample was recrystallized from ether/hexanes. mp 48.5-49.5° C.; $[\alpha]^{25}_D$=−63.1 (c 0.89, CHCl$_3$); IR (neat) 3470 cm$^{-1}$; $^1$H NMR (CDCl$_3$) δ 7.38 (5H, s), 5.00-5.06 (1H, m), 3.44-3.49 (2H, m), 3.26 (3H, s), 2.60 (1H, br s); $^{13}$C NMR (CDCl$_3$) δ 141.5, 128.7, 128.5, 125.9, 73.0, 50.5, 44.8; HRMS (FAB+) m/z: calcd for C$_9$H$_{12}$O$_3$S$_2$+H, 233.0307; found, 233.0326.

(S)-2-hydroxy-2-phenyl-ethylmethanethiosulfonate ((S)-1b)

(S)-4 was prepared in the same manner as (R)-4. From (S)-mandelic acid (3.176 g, 20.87 mmol) was obtained crude (S)-4 (3.45 g, quantitative) which was used directly in the next step.

(S)-5 was prepared in the same manner as (R)-5. From (S)-4 (3.45 g, 20.76 mmol) was obtained (S)-5 (3.014 g, 69%). Its $^1$H NMR and $^{13}$C NMR data were identical to (R)-5. $[\alpha]^{25}_D$=+131.6 (c 1.74, CHCl$_3$).

(S)-7, was prepared in the same manner as (R)-7. From (S)-5 (2.995 g, 14.25 mmol) was obtained (S)-7 (2.565 g, 99%) Its $^1$H NMR and $^{13}$C NMR data were identical to (R)-7. $[\alpha]^{25}_D$=+193.2 (c 1.30, CHCl$_3$).

(S)-9 was prepared in the same manner as (R)-9. From (S)-7 (2.467 g, 13.54 mmol) was obtained (S)-9 (3.486 g, 99%). Its $^1$H NMR and $^{13}$C NMR data were identical to (R)-9. $[\alpha]^{25}_D$=+135.5 (c 1.40, CHCl$_3$).

(S)-11, was prepared in the same manner as (R)-11. From (S)-9 (3.486 g, 13.39 mmol) was obtained (S)-11 (2.822 g, 86%). Its $^1$H NMR and $^{13}$C NMR data were identical to (R)-11. $[\alpha]^{25}_D$=+125.8 (c 1.21, MeOH).

(S)-12 was prepared in the same manner as (R)-12. From (S)-11 (0.863 g, 3.521 mmol) was obtained (S)-12 (0.541 g, 56%). Its $^1$H NMR and $^{13}$C NMR data were identical to (R)-12. $[\alpha]^{25}_D$=+153.4 (c 2.43, CHCl$_3$).

The title compound, (S)-1b, was prepared in the same manner as (R)-1b. From (S)-12 (0.526 g, 1.903 mmol) was obtained (S)-1b (0.419 g, 95%, ee≧98%), as white crystals which were recrystallized from ether/hexanes. Its $^1$H NMR and $^{13}$C NMR data were identical to (R)-1b. mp 47.0-48.0° C.; $[\alpha]^{25}_D$=+63.3 (c 1.676, CHCl$_3$); HRMS (FAB+) m/z: calcd for C$_9$H$_{12}$O$_3$S$_2$+H, 233.0307.

N-(3'-methanethiosulfonatopropyl)-2-oxazolidinone (1c)

To a cooled solution (15-20° C.) of 1,3-dibromopropane (6.4 mL, 63.05 mmol) in dry DMSO (5 mL) was added ground KOH (0.920 g, 16.40 mmol). 2-Oxazolidinone (1.100 g, 12.63 mmol) was added in small amounts over 5 min, and the reaction was stirred for 4 hr at 20° C. The mixture was diluted with ether (100 mL) and H$_2$O (20 mL), and the aqueous phase was extracted with ether (3×50 mL). After drying with MgSO$_4$, the crude product was purified by flash chromatography using a step gradient (25% EtOAc/75% hexanes to 50% EtOAc/50% hexanes) to give N-(3'-bromopropyl)-2-oxazolidinone, 17 (1.48 g, 56%). IR (neat) 1747 cm$^{-1}$; $^1$H NMR (CDCl$_3$) δ 4.30 (2H, t, J=7.2 Hz), 3.57 (2H, t, J=8.2 Hz), 3.33-3.43 (4H, q), 2.03-2.17 (2H, m); $^{13}$C NMR (CDCl$_3$) δ 158.4, 61.7, 45.0, 43.0, 30.4, 29.9; HRMS (FAB+) m/z: calcd for C$_6$H$_{10}$NO$_2$Br, 207.9972; found, 207.9957.

The title compound, 1c, was prepared in the same manner as (R)-1a. 17 (1.316 g, 6.325 mmol) was converted to 1c (1.013 g, 67%). It was recrystallized from EtOAc/ether. mp 36-37.5° C.; IR (neat) 1748 cm$^{-1}$; $^1$H NMR (CDCl$_3$) δ 4.32 (2H, t, J=7.4 Hz), 3.56 (2H, t, J=8.4 Hz), 3.35 (2H, t, J=6.7 Hz), 3.31 (3H, s), 3.14 (2H, t, J=7.0 Hz), 1.96-2.10 (2H, m); $^{13}$C NMR (CDCl$_3$) δ 158.5, 61.7, 50.4, 44.6, 42.9, 33.2, 27.6; HRMS (FAB+) m/z: calcd for C$_7$H$_{13}$NO$_4$S$_2$+H, 240.0364; found, 240.0365.

N-(3'-methanethiosulfonatopropyl)-(R)-4-isopropyl-2-oxazolidinone ((R)-1d)

N-(3'-bromopropyl)-(R)-4-isopropyl-2-oxazolidinone, (R)-18, was prepared in the same manner as 17. From (R)-4-isopropyl-2-oxazolidinone (0.518 g, 4.011 mmol) was obtained (R)-18 (0.626 g, 62%, ee≧98%), as a colorless oil. [α]$^{25}_D$=−2.7 (c 1.87, CHCl$_3$); IR (neat) 1748 cm$^{-1}$; $^1$H NMR (CDCl$_3$) δ 4.20 (1H, t, J=8.8 Hz), 4.04 (1H, dd, J=9.0, 5.3), 3.69-3.77 (1H, m), 3.47-3.58 (1H, m), 3.40 (2H, t, J=6.5 Hz), 3.06-3.20 (1H, m), 2.25-1.99 (3H, m), 0.86 (6H, t, J=7.4 Hz); $^{13}$C NMR (CDCl$_3$) δ 158.3, 62.7, 59.6, 40.6, 30.2, 27.7, 17.5, 14.2; HRMS (FAB+) m/z: calcd for C$_9$H$_{16}$NO$_2$Br, 250.0441; found, 250.0419.

The title compound, (R)-1d was prepared in the same manner as (R)-1a. (R)-18 (0.530 g, 2.119 mmol) was converted to (R)-1d (0.492 g, 83%). [α]$^{25}_D$=−22.3 (c 1.37, CHCl$_3$); IR (neat) 1744 cm$^{-1}$; $^1$H NMR (CDCl$_3$) δ 4.25 (1H, t, J=9.0 Hz), 4.07 (1H, dd, J=9.0, 5.4 Hz), 3.73-3.81 (1H, m), 3.50-3.65 (1H, m), 3.33 (3H, s), 3.07-3.21 (3H, m), 1.98-2.13 (3H, m), 0.90 (3H, d, J=7.0 Hz), 0.86 (3H, d, J=6.8 Hz); $^{13}$C NMR (CDCl$_3$) δ 158.6, 62.9, 59.2, 50.5, 40.5, 33.5, 27.9, 27.6, 17.6, 14.2; HRMS (FAB+) m/z: calcd for C$_{10}$H$_{19}$NO$_4$S$_2$+H, 282.0834; found, 282.0842.

N-(3'-methanethiosulfonatopropyl)-(S)-4-isopropyl-2-oxazolidinone ((S)-1d)

(S)-18 was prepared in the same manner as (R)-18. From (S)-4-isopropyl-2-oxazolidinone (0.504 g, 3.902 mmol) was obtained (S)-18 (0.558 g, 57%, ee≧98%)). Its $^1$H NMR and $^{13}$C NMR data were identical to (R)-18. [α]$^{25}_D$=+3.4 (c 3.42, CHCl$_3$).

The title compound, (S)-1d, was prepared in the same manner as (R)-1d. From (S)-18 (0.493 g, 1.971 mmol) was obtained (S)-1d (0.435 g, 78%). Its $^1$H NMR and $^{13}$C NMR data were identical to (R)-1d. [α]$^{25}_D$=+23.2 (2.27, CHCl$_3$); HRMS (EI) m/z: calcd for C$_{10}$H$_{19}$NO$_4$S$_2$+H, 282.0834; found, 282.0833.

N-(3'-methanethiosulfonatopropyl)-(R)-4-phenyl-2-oxazolidinone ((R)-1e)

N-(3'-bromopropyl)-(R)-4-phenyl-2-oxazolidinone, (R)-19, was prepared in the same manner as 17. From (R)-4-phenyl-2-oxazolidinone (0.322 g, 1.970 mmol) was obtained (R)-19 (0.370 g, 66%, ee≧98%), as a colorless oil. [α]$^{25}_D$=−35.8 (c 3.10, CHCl$_3$); IR (neat) 1748 cm$^{-1}$; $^1$H NMR (CDCl$_3$) δ 7.26-7.45 (5H, m), 4.79 (1H, dd, J=8.8, 6.3 Hz), 4.63 (1H, dd, J=8.6, 8.6 Hz), 4.15 (1H, dd, J=8.6, 6.4 Hz), 3.30-3.54 (3H, m), 2.89-3.03 (1H, m), 1.90-2.12 (2H, m); $^{13}$C NMR (CDCl$_3$) δ 158.2, 137.7, 129.3, 129.2, 126.9, 69.8, 60.3, 41.1, 30.2, 29.9; HRMS (EI) m/z: calcd for C$_{12}$H$_{14}$NO$_2$Br, 283.0208; found, 283.0197.

The title compound, (R)-1e, was prepared in the same manner as (R)-1a. (R)-19 (0.346 g, 1.218 mmol) was converted to (R)-1e (0.344 g, 89%). [α]$^{25}_D$=−70.5 (c 0.84, CHCl$_3$); IR (neat) 1746 cm$^{-1}$; $^1$H NMR (CDCl$_3$) δ 7.26-7.43 (5H, m), 4.81 (1H, dd, J=8.8, 6.6 Hz), 4.65 (1H, dd, J=8.6, 8.6 Hz), 4.16 (1H, dd, J=8.6, 6.6 Hz), 3.40-3.55 (1H, m), 3.29 (3H, s), 2.90-3.15 (3H, m), 1.82-1.97 (2H, m); $^{13}$C NMR (CDCl$_3$) δ 158.4, 137.5, 129.4, 129.3, 127.1, 69.9, 60.0, 50.6, 41.0, 33.4, 27.5; HRMS (FAB+) m/z: calcd for C$_{13}$H$_{17}$NO$_4$S$_2$+H, 316.0678; found, 316.0678.

N-(3'-methanethiosulfonatopropyl)-(S)-4-phenyl-2-oxazolidinone ((S)-1e)

(S)-19 was prepared in the same manner as (R)-19. From (S)-4-phenyl-2-oxazolidinone (0.964 g, 5.911 mmol) was obtained (S)-19 (0.955 g, 57%, ee≧98%)). Its $^1$H NMR and $^{13}$C NMR data were identical to (R)-19. [α]$^{25}_D$=+33.3 (c 2.50, CHCl$_3$).

The title compound, (S)-1e, was prepared in the same manner as (R)-1e. From (S)-19 (0.870 g, 3.062 mmol) was obtained (S)-1e (0.814 g, 84%). Its $^1$H NMR and $^{13}$C NMR data were identical to (R)-1e. [α]$^{25}_D$=+68.8 (1.21, CHCl$_3$); HRMS (EI) m/z: calcd for C$_{13}$H$_{17}$NO$_4$S$_2$+H, 316.0678; found, 316.0683.

N-(3'-methanethiosulfonatopropyl)-(R)-4-benzyl-2-oxazolidinone ((R)-1f)

N-(3'-bromopropyl)-(R)-4-benzyl-2-oxazolidinone, (R)-20, was prepared in the same manner as 17. From (R)-4-benzyl-2-oxazolidinone (0.499 g, 2.816 mmol) was obtained (R)-20 (0.454 g, 54%, ee≧98%), as a colorless oil. [α]$^{25}_D$=−14.3 (c 2.06, CHCl$_3$); IR (neat) 1751 cm$^{-1}$; $^1$H NMR (CDCl$_3$) δ 7.14-7.36 (5H, m), 3.96-4.21 (3H, m), 3.10-3.65 (5H, m), 2.61-2.72 (1H, m), 2.04-2.27 (2H, m); $^{13}$C NMR (CDCl$_3$) δ 158.0, 135.2, 128.9, 128.8, 127.1, 66.7, 56.6, 40.8, 38.5, 30.5, 30.2; HRMS (FAB+) m/z: calcd for C$_{13}$H$_{16}$NO$_2$Br, 298.0441; found, 298.0416.

The title compound, (R)-1f, was prepared in the same manner as (R)-1a. (R)-20 (0.364 g, 1.221 mmol) was converted to (R)-1f (0.362 g, 90%). [α]$^{25}_D$=−31.7 (c 1.33, CHCl$_3$); IR (neat) 1745 cm$^{-1}$; $^1$H NMR (CDCl$_3$) δ 7.14-7.34 (5H, m), 3.98-4.21 (3H, m), 3.48-3.61 (1H, m), 3.32 (3H, s), 3.04-3.30 (4H, m), 2.61-2.73 (1H, m), 1.98-2.11 (2H, m); $^{13}$C NMR (CDCl$_3$) δ 158.2, 135.2, 128.9, 128.8, 127.1, 66.7, 56.1, 50.4, 40.7, 38.4, 33.3, 27.8; HRMS (FAB+) m/z: calcd for C$_{14}$H$_{19}$NO$_4$S$_2$+H, 330.0834; found, 330.0834.

N-(3'-methanethiosulfonatopropyl)-(S)-4-benzyl-2-oxazolidinone ((S)-1f)

(S)-20 was prepared in the same manner as (R)-20. From (S)-4-benzyl-2-oxazolidinone (0.504 g, 2.844 mmol) was obtained (S)-20 (0.558 g, 66%, ee≧98%)). Its $^1$H NMR and $^{13}$C NMR data were identical to (R)-20. [α]$^{25}_D$=+14.1 (c 2.50, CHCl$_3$).

The title compound, (S)-1f, was prepared in the same manner as (R)-1f. From (S)-20 (0.449 g, 1.506 mmol) was obtained (S)-1f (0.458 g, 92%). Its $^1$H NMR and $^{13}$C NMR data were identical to (R)-1f. $[\alpha]^{25}_D$=+29.9 (1.19, CHCl$_3$); HRMS (EI) m/z: calcd for C$_{14}$H$_{19}$NO$_4$S$_2$+H, 330.0834; found, 330.0844.

N-(2'-methanethiosulfonatoethyl)-(R)-4-phenyl-2-oxazolidinone ((R)-1g)

N-(3'-bromoethyl)-(R)-4-phenyl-2-oxazolidinone, (R)-21, was prepared in the same manner as 17, except 10 eq of 1,2-dibromoethane and 3 eq of KOH were used. From (R)-4-phenyl-2-oxazolidinone (0.261 g, 1.599 mmol) was obtained (R)-21 (0.387 g, 90%, ee≧98%), as a colorless oil. $[\alpha]^{25}_D$=−54.1 (c 1.80, CHCl$_3$); IR (neat) 1749 cm$^{-1}$; $^1$H NMR (CDCl$_3$) δ 7.26-7.46 (5H, m), 4.98 (1H, dd, J=8.8, 6.6 Hz), 4.67 (1H, dd, J=8.8, 8.8 Hz), 4.16 (1H, dd, J=8.8, 6.6 Hz), 3.75-3.87 (1H, m), 3.42-3.53 (1H, m), 3.12-3.36 (2H, m); $^{13}$C NMR (CDCl$_3$) δ 158.0, 137.4, 129.4, 129.3, 127.0, 70.0, 60.4, 43.8, 28.6; HRMS (EI) m/z: calcd for C$_{11}$H$_{12}$NO$_2$Br, 269.0051; found, 269.0055.

The title compound, (R)-1g, was prepared in the same manner as (R)-1a. (R)-21 (0.392 g, 1.462 mmol) was converted to (R)-1g (0.320 g, 73%). $[\alpha]^{25}_D$=−28.8 (c 1.32, CHCl$_3$); IR (neat) 1749 cm$^{-1}$; $^1$H NMR (CDCl$_3$) δ 7.29-7.43 (5H, m), 4.88 (1H, dd, J=8.9, 6.6 Hz), 4.67 (1H, dd, J=8.8, 8.8 Hz), 4.18 (1H, dd, J=8.8, 6.5 Hz), 3.59-3.76 (1H, m), 3.28 (3H, s), 3.10-3.26 (3H, m); $^{13}$C NMR (CDCl$_3$) δ 158.1, 137.3, 129.4, 129.3, 127.1, 69.9, 60.3, 50.7, 41.8, 33.6; HRMS (EI) m/z: calcd for C$_{12}$H$_{15}$NO$_4$S$_2$+H, 302.0521; found, 302.0529.

N-(2'-methanethiosulfonatoethyl)-(S)-4-phenyl-2-oxazolidinone ((S)-1g)

(S)-21, was prepared in the same manner as (R)-21. From (S)-4-phenyl-2-oxazolidinone (0.381 g, 2.335 mmol) was obtained (S)-21 (0.564 g, 89%, ee≧98%)). Its $^1$H NMR and $^{13}$C NMR data were identical to (R)-21. $[\alpha]^{25}_D$=+54.6 (c 1.85, CHCl$_3$).

The title compound, (S)-1g, was prepared in the same manner as (R)-1g. From (S)-21 (0.532 g, 1.969 mmol) was obtained (S)-1g (0.450 g, 76%). Its $^1$H NMR and $^{13}$C NMR data were identical to (R)-1g. $[\alpha]^{25}_D$=+27.8 (1.30, CHCl$_3$); HRMS (EI) m/z: calcd for C$_{12}$H$_{15}$NO$_4$S$_2$+H, 302.0521; found, 302.0534.

N-(2'-methanethiosulfonatoethyl)-(R)-4-benzyl-2-oxazolidinone ((R)-1h)

N-(3'-bromoethyl)-(R)-4-benzyl-2-oxazolidinone, (R)-22, was prepared in the same manner as 17, except 10 eq of 1,2-dibromoethane and 3 eq of KOH were used. From (R)-4-benzyl-2-oxazolidinone (0.386 g, 2.178 mmol) was obtained (R)-22 (0.372 g, 60%, ee≧98%), as a colorless oil. $[\alpha]^{25}_D$=−16.7 (c 1.35, CHCl$_3$); IR (neat) 1748 cm$^{-1}$; $^1$H NMR (CDCl$_3$) δ 7.12-7.40 (5H, m), 3.81-4.30 (4H, m), 3.38-3.63 (3H, m), 3.11-3.20 (1H, m), 2.66-2.76 (1H, m); $^{13}$C NMR (CDCl$_3$) δ 157.8, 135.2, 129.0, 127.3, 67.1, 56.9, 44.1, 38.7, 29.1; HRMS (EI) m/z: calcd for C$_{12}$H$_{14}$NO$_2$Br, 284.0286; found, 284.0281.

The title compound, (R)-1h, was prepared in the same manner as (R)-1a. (R)-22 (0.334 g, 1.175 mmol) was converted to (R)-1h (0.363 g, 98%). $[\alpha]^{25}_D$=+4.5 (c 1.10, CHCl$_3$); IR (neat) 1748 cm$^{-1}$; $^1$H NMR (CDCl$_3$) δ 7.15-7.39 (5H, m), 4.02-4.29 (3H, m), 3.72-3.89 (1H, m), 3.14-3.58 (4H, m), 3.38 (3H, s), 2.65-2.75 (1H, m); $^{13}$C NMR (CDCl$_3$) δ 158.1, 135.2, 129.0, 127.3, 67.2, 57.0, 50.7, 42.0, 38.7, 33.9; HRMS (EI) m/z: calcd for C$_{13}$H$_{17}$NO$_4$S$_2$+H, 316.0677; found, 316.0683.

N-(2'-methanethiosulfonatoethyl)-(S)-4-benzyl-2-oxazolidinone ((S)-1h)

(S)-22 was prepared in the same manner as (R)-22. From (S)-4-benzyl-2-oxazolidinone (0.371 g, 2.094 mmol) was obtained (S)-22 (0.375 g, 63%, ee≧98%)). Its $^1$H NMR and $^{13}$C NMR data were identical to (R)-22. $[\alpha]^{25}_D$=+15.6 (c 1.55, CHCl$_3$).

The title compound, (S)-1h, was prepared in the same manner as (R)-1h. From (S)-22 (0.328 g, 1.154 mmol) was obtained (S)-1h (0.245 g, 67%). Its $^1$H NMR and $^{13}$C NMR data were identical to (R)-1h. $[\alpha]^{25}_D$=−5.8 (c 1.20, CHCl$_3$); HRMS (EI) m/z: calcd for C$_{13}$H$_{17}$NO$_4$S$_2$+H, 316.0677; found, 316.0664.

N-(3'-methanethiosulfonatopropyl)-(3aR-cis)-3,3a,8,8a-tetrahydro-2H-indeno[1,2-d]-oxazol-2-one ((R)-1i)

(1R,2S)-cis-1-amino-2-indanol (0.980 g, 6.569 mmol) was placed in a round-bottomed flask and a dry Ar atmosphere was established. Dry CH$_2$Cl$_2$ (50 mL) and Et$_3$N (1.9 mL, 13.63 mmol) were added, and the resulting solution was cooled to −60° C. On addition of triphosgene (0.64 g, 2.157 mmol), the cooling bath was removed, and the reaction was allowed to warm to 20° C. over one hour. The reaction was then poured into CH$_2$Cl$_2$ (100 mL) and H$_2$O (50 mL) and the aqueous phase was extracted with CH$_2$Cl$_2$ (3×100 mL). After drying with MgSO$_4$, the organic layer was evaporated under reduced pressure to give (3aR-cis)-3,3a,8,8a-tetrahydro-2H-indeno[1,2-d]-oxazol-2-one, (R)-24 (1.15 g, quantitative) as white crystals, which was of sufficient purity for the next step in the reaction sequence. An analytical sample was recrystallized from CH$_2$Cl$_2$/hexanes. mp 205.5-206.5° C.; [Ghosh et al. (1992) *J. Chem. Soc. Chem. Commun.* 1673-1674 for enantiomer mp 205° C.]; $[\alpha]^{25}_D$=+107.7 (c 1.25, CHCl$_3$); [Id. for enantiomer $[\alpha]^{25}_D$=−79.4 (c 1.4, CHCl$_3$)]. IR (KBr) 3255, 1752, 1707 cm$^{-1}$; $^1$H NMR (acetone-d6) δ 7.24-7.43 (4H, m), 5.39 (1H, t, J=7.5 Hz), 5.21 (1H, d, J=7.0 Hz), 3.42 (1H, dd, J=17.7, 6.2 Hz), 3.20 (1H, d, J=17.9 Hz), 2.90 (1H, br s); $^{13}$C NMR (acetone-d6) δ 159.1, 142.5, 141.0, 129.7, 128.3, 126.2, 125.8, 80.8, 61.7, 39.3; HRMS (FAB+) m/z: calcd for C$_{10}$H$_9$NO$_2$+H, 176.0771; found, 176.0681.

N-(3'-bromopropyl)-(3aR-cis)-3,3a,8,8a-tetrahydro-2H-indeno[1,2-d]-oxazol-2-one, (R)-25, was prepared in the same manner as 17. From (R)-24 (1.007 g, 5.748 mmol) was obtained (R)-25 (1.11 g, 65%, ee≧98%), as a colorless oil. $[\alpha]^{25}_D$=+31.3 (c 1.61, CHCl$_3$); IR (neat) 1748 cm$^{-1}$; $^1$H NMR (CDCl$_3$) δ 7.24-7.45 (4H, m), 5.31 (1H, dt, J=7.4, 3.1 Hz), 5.14 (1H, d, J=7.7 Hz), 3.23-3.70 (6H, m), 2.12-2.34 (2H, m); $^{13}$C NMR (CDCl$_3$) δ 157.1, 140.5, 138.0, 129.8, 127.4, 125.8, 125.1, 77.1, 64.1, 41.0, 39.3, 30.4, 30.1; HRMS (FAB+) m/z: calcd for C$_{13}$H$_{14}$NO$_2$Br, 296.0285; found, 296.0254.

The title compound, (R)-1i, was prepared in the same manner as (R)-1a. (R)-25 (0.925 g, 3.123 mmol) was converted to (R)-1i (0.882 g, 86%). It was recrystallized from EtOAc/hexanes. mp 94.0-95.0° C.; $[\alpha]^{25}_D$=+17.7 (c 1.28, CHCl$_3$); IR (KBr) 1729 cm$^{-1}$; $^1$H NMR (CDCl$_3$) δ 7.26-7.38 (4H, m), 5.32 (1H, dt, J=7.4, 3.0 Hz), 5.14 (1H, d, J=7.6 Hz), 3.36-3.69 (4H, m), 3.32 (3H, s), 3.14-3.22 (2H, m), 2.10-2.23 (2H, m); $^{13}$C NMR (CDCl$_3$) δ 157.2, 140.6, 137.9, 129.7, 127.4, 125.8, 125.0, 77.2, 63.7, 50.4, 40.9, 39.2, 33.4, 27.5; HRMS (FAB+) m/z: calcd for C$_{14}$H$_{17}$NO$_4$S$_2$+H, 328.0677; found, 328.0683.

N-(3'-methanethiosulfonatopropyl)-(3aS-cis)-3,3a,8,8a-tetrahydro-2H-indeno[1,2-d]-oxazol-2-one ((S)-1i)

(S)-24 was prepared in the same manner as (R)-24. From (1S,2R)-cis-1-amino-2-indanol (1.09 g, 7.306 mmol) was obtained (S)-24 (1.27 g, quantitative). Its $^1$H NMR and $^{13}$C NMR data were identical to (R)-24. mp 205.0-207.0° C.; $[\alpha]^{25}_D = -109.7$ (c 1.30, CHCl$_3$).

(S)-25 was prepared in the same manner as (R)-25. From (S)-24 (1.023 g, 5.839 mmol) was obtained (S)-25 (0.940 g, 54%, ee≧98%). Its $^1$H NMR and $^{13}$C NMR data were identical to (R)-25. $[\alpha]^{25}_D = -30.5$ (c 1.82, CHCl$_3$).

The title compound, (S)-1i, was prepared in the same manner as (R)-1i. From (S)-25 (0.840 g, 2.836 mmol) was obtained (S)-1i (0.838 g, 90%). It was recrystallized from EtOAc/hexanes. Its $^1$H NMR and $^{13}$C NMR data were identical to (R)-1i. mp 94.0-95.0° C.; $[\alpha]^{25}_D = -18.7$ (c 1.38, CHCl$_3$); HRMS (EI) m/z: calcd for $C_{14}H_{17}NO_4S_2$+H, 328.0677; found, 328.0694.

Site-Specific Chemical Modification

To 1.25 mL of a SBL mutant stored in MES buffer (10 mM MES, 1 mM CaCl$_2$, pH 5.8) was added 0.75 mL CHES buffer (70 mM CHES, 5 mM MES, 2 mM CaCl$_2$, pH 9.5) at 20° C. and one of the methanethiosulfonate reagents (100 μL of a 0.5 M solution in CH$_3$CN) in a PEG (10,000) coated polypropylene test tube, and the mixture agitated in an end-over-end rotator. After 30 min, all modification reactions were negative to the Ellman's test indicating the absence of free thiol. In order to ensure complete reaction, a further 100 μL of methanethiosulfonate solution was added and the reaction was continued for another 30 min. The reaction solution was purified on a disposable desalting column (Pharmacia Biotech PD-10, Sephadex G-25 M) pre-equilibrated with MES buffer (5 mM MES, 2 mM CaCl$_2$, pH 6.5). The CMM was eluted with MES-buffer (5.0 mL), dialyzed (MWCO 12-14, 000) against MES buffer (10 mM MES, 1 mM CaCl$_2$, pH 5.8) then flash frozen and stored at -20° C. Modified enzymes were analyzed by nondenaturing gradient (8-25%) gels at pH 4.2, run towards the cathode on the Pharmacia Phast-Systemä, (Pharmacia Application File No. 300) and appeared as one single band. Each of the CMMs was analyzed in parallel with its parent cysteine mutant and the WT enzyme.

Enzyme Characterization

Prior to ES-MS analysis, CMMs were purified by FPLC (BioRad, Biologic System) on a Source 15 RPC matrix (17-0727-20 from Pharmacia) with 5% acetonitrile, 0.01% TFA as the running buffer and eluted with 80% acetonitrile, 0.01% TFA in a one step gradient. Electrospray mass spectra were recorded on a PE SCIEX API III Biomolecular Mass Analyzer.

TABLE 3

Electro-spray Mass Spectra of CMMs[a]

| Enzyme | Calculated Mass (R) | Calculated Mass (S) | Found Mass (R) | Found Mass (S) |
|---|---|---|---|---|
| N62C-a | 26853 | 26853 | 26855 | 26854 |
| N62C-b | 26839 | 26839 | 26841 | 26838 |
| N62C-c | 26846 | | 26850 | |
| N62C-d | 26888 | 26888 | 26889 | 26889 |
| N62C-e | 26922 | 26922 | 26921 | 26921 |
| N62C-f | 26936 | 26936 | 26939 | 26939 |
| N62C-g | 26908 | 26908 | 26910 | 26907 |
| N62C-h | 26922 | 26922 | 26924 | 26924 |
| N62C-i | 26934 | 26934 | 26937 | 26936 |
| S166C-a | 26880 | 26880 | 26881 | 26886 |
| S166C-b | 26866 | 26866 | 26862 | 26872 |
| S166C-c | 26873 | | 26877 | |
| S166C-d | 26915 | 26915 | 26915 | 26916 |
| S166C-e | 26949 | 26949 | 26950 | 26951 |
| S166C-f | 26963 | 26963 | 26964 | 26963 |
| S166C-g | 26935 | 26935 | 26937 | 26934 |

TABLE 3-continued

Electro-spray Mass Spectra of CMMs[a]

| Enzyme | Calculated Mass (R) | Calculated Mass (S) | Found Mass (R) | Found Mass (S) |
|---|---|---|---|---|
| S166C-h | 26949 | 26949 | 26951 | 26949 |
| S166C-i | 26961 | 26961 | 26964 | 26964 |
| L217C-a | 26854 | 26854 | 26850 | 26850 |
| L217C-b | 26840 | 26840 | 26842 | 26840 |
| L217C-c | 26847 | | 26847 | |
| L217C-d | 26889 | 26889 | 26892 | 26892 |
| L217C-e | 26923 | 26923 | 26922 | 26923 |
| L217C-f | 26937 | 26937 | 26938 | 26940 |
| L217C-i | 26935 | 26935 | 26937 | 26937 |
| S156C-a | 26880 | 26880 | 26883 | 26883 |
| S156C-d | 26866 | 26866 | 26866 | 26868 |
| S156C-e | 26949 | 26949 | 26949 | 26949 |

[a]mol. wt. ± 6 mass units in all cases

The free thiol content of N62C, L217C, S166C, S156C and their CMMs, was determined spectrophotometrically by titration with Ellman's reagent ($\epsilon_{412}=13600$ M$^{-1}$ cm$^{-1}$) (Ellman et al., (1961) *Biochem. Pharmacol.*, 7: 88-95) phosphate buffer 0.25 M, pH 8.0.

The active enzyme concentration was determined as previously described (Hsia et al. (1996) *Anal. Biochem.* 242: 221-227) by monitoring fluoride release upon enzyme reaction with a-toluenesulfonyl fluoride (Aldrich Chemical Co. Inc.) as measured by a fluoride ion sensitive electrode (Orion Research 96-09). The active enzyme concentration determined in this way was used to calculate kinetic parameters for each CMM.

Kinetic Measurements

Specificity constants determined using the low substrate approximation were measured at 0.05 and 0.1 mM N-Suc-AAPF-pNA at 25° C. in 0.1 M Tris containing 0.005% Tween 80 and 1% DMSO at pH 8.6 for amidase activity ($\epsilon_{410}=8800$ M$^{-1}$ cm$^{-1}$), and at 0.015 and 0.03 mM N-Suc-AAPF-SBn at 25° C. in 0.1 M Tris containing 0.005% Tween 80 and 1% 37.5 mM DTNB in DMSO at pH 8.6 for esterase activity ($\epsilon_{412}=13600$ M$^{-1}$ cm$^{-1}$). A general run consisted of equilibrating six plastic cuvettes containing 980 μL of 0.1 M Tris, 0.005% Tween 80 at pH 8.6 to 25° C. The substrate (10 μL) in DMSO was added and the cuvette was shaken twice before returning it to the machine for zeroing. Immediately, the enzyme (10 μL) in 20 mM MES, 1 mM CaCl$_2$ at pH 5.8 was added and the cuvette was returned to the machine with a eight sec delay. The initial rate data was recorded and used to calculate $k_{cat}/K_M$. Esterase data was adjusted to account for background hydrolysis of the substrate.

Michaelis-Menten constants were measured at 25° C. by curve fitting (GraFit® 3.03) of the initial rate data determined at eight concentrations (0.05 mM-3.0 mM) of the N-Suc-AAPF-pNA substrate for amidase activity and eight concentrations (0.015 mM-2.0 mM) of the N-Suc-AAPF-SBn substrate for esterase activity.

Example 2

Chemically Modified Mutants of Subtilisin *Bacillus lentus* Catalyze Transesterification Reactions Better than Wild Type In this example, a combined site-directed mutagenesis and chemical modification strategy was used to create superior enzyme catalysts for the resolution of racemic primary and secondary alcohols using a transesterification reaction. The chemically modified mutant N62C—S—CH$_3$ of subtilisin *Bacillus lentus* catalyzes the transesterification of N-acetyl-L-phenylalanine vinyl ester with β-branched primary alcohols faster than wild type. The cysteine mutant, M222C of subtilisin *Bacillus lentus* gave higher yields (90% and 92% yields with 1-phenylethanol and 2-octanol respectively versus 19% and 10% for wild-type) and better enantioselectivity than wild-type when secondary alcohols were used.

Figure 8:
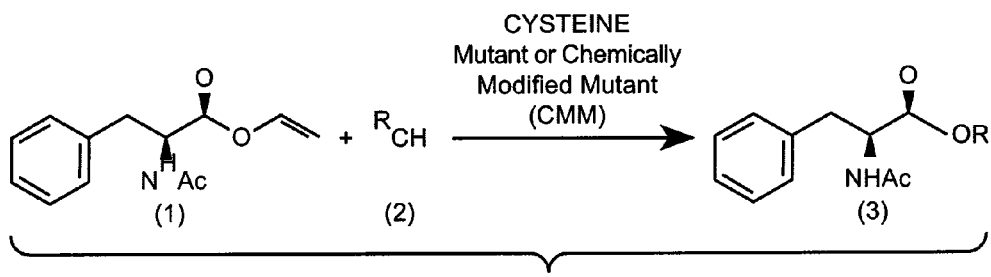
FIG. 8 illustrates a reaction scheme for the transesterification of N-acetyl-1-phenylalanine vinyl ester with an alcohol using a chemically modified mutant enzyme as a catalyst.

Hydrolase-catalyzed transesterifications are widely employed to resolve racemic alcohols and to stereoselectively acylate prochiral and meso diols (Faber (1996) *Biotransformations in Organic Chemistry*, 3rd Ed., Springer-Verlag, Heidelberg). In this regard, serine proteases have found limited application in comparison to lipases and esterases (Id.). One reason for this is the high substrate specificity of many serine proteases compared to other hydrolases (Faber supra., Sears and Wong (1996) *Biotechnol. Prog.*, 12: 423-433). Recently, in an effort to extend the synthetic potential of the serine protease subtilisin *Bacillus lentus* (SBL), we reported the use of N—Ac-L-Phe vinyl ester, 2 (FIG. 8), as an acyl donor SBL-catalyzed transesterification reactions with racemic alcohols (Lloyd et al. (1998) *Tetrahedron Asymmetry*, 9: 551-561). This example illustrates the potential for improving the overall chemical yield and degree of stereoselectivity for these resolutions using a combined site directed mutagenesis and chemical modification strategy to alter the substrate specificity of SBL.

Cysteine mutants of SBL and chemically modified mutants (CMMs) were prepared and characterized as described above and in Berglund et al. (196) *Bioorg. Med. Chem. Lett.*, 6: 2507-2512) and the best esterases among them were selected for comparative evaluation (Plettner et al. (198) *Bioorg. Med. Chem. Lett.*, 8: 2291-2296). Three CMMs (L217C—S—(CH$_2$)$_2$—SO$_3$—, N62C—S—(CH$_2$)$_2$—SO$_3$—, N62C—S—CH$_3$) and two mutant enzymes (L217C and M222C) were each embedded in a KCl matrix (Khmelnitsky et al. (1994) *J. Am. Chem. Soc.*, 116: 2647-2648) and used to catalyze transesterification reactions in tert-BuOH between the acyl donor, 2, and racemic primary and secondary alcohols, 1 FIG. 8, as previously described Lloyd et al. (1998) *Tetrahedron Asymmetry*, 9: 551-561). Two primary alcohols (2-phenyl-1-propanol and 2-methyl-1-pentanol) and 1 secondary alcohol (2-octanol) were used as representative nucleophiles for the study. The results are given in Table 4. L217C ante L217C—S—(CH$_2$)$_2$—SO$_3^-$ CMM catalyzed the reaction with two primary alcohols in similar yields and de's to wild-type (WT), but only L217C gave as good a yield as WT using 2-octanol as nucleophile. M222C gave lower yields for all 3 alcohols. N62C—S—(CH$_2$)$_2$—SO$_3^-$ gave a higher yield of product than WT when 2-phenyl-1-propanol was the nucleophile. For the reaction with 2-methyl-1-penatanol, using N52-C—S—(CH$_2$)$_2$—SO$_3^-$ as catalyst gave a significant improvement in the des of the product ester (41%) over WT (26% de). Only one CMM catalyst, N62C—S—CH$_3$, gave marked increases in product yield for the two primary alcohols (97% for 2-phenyl-1-propanol and 79% for 2-methyl-1-pentanol). No changes in stereochemical preferences from WT were observed for any of the CMMs.

TABLE 4

Yields and d.e. values of 3 from mutant and CMM-catalyzed reactions in t-BuOH at 50° C.

| Enzyme | 2-phenyl-1 propanol | | | 2-methyl-1-pentanol | | | 2-octanol | | |
|---|---|---|---|---|---|---|---|---|---|
| | % yield | % de | Abs. Conf. | % yield | % de | Abs. Conf. | % yield | % de | Abs. Conf. |
| WT[3] | 53 | 30 | R | 58 | 26 | R | 20 | >99 | S |
| M222C | 20 | 29 | R | 18 | 21 | R | 9 | >99 | S |
| L217C | 59 | 22 | R | 50 | 12 | R | 19 | >99 | S |
| L217C—S—(CH$_2$)$_2$—SO$_3^-$ | 49 | 30 | R | 29 | 17 | R | <5 | — | S |
| N62C—S—(CH$_2$)$_2$—SO$_3^-$ | 65 | 32 | R | 59 | 41 | R | 8 | >99 | S |
| N62C—CH$_3$ | 97 | 24 | R | 79 | 34 | R | 16 | >99 | S |

Conditions:

All reactions used 10 equiv. of alcohol, 1, and the acyl donor, 2, in t-BuOH at 50° C. for 24 hr (primary alcohols) or for 72 hours (secondary alcohols) as previously described (Lloyd et al. (1998) *Tetrahedron Asymmetry*, 9: 551-561). All yields and diastereomeric excess (d.e.) (HPLC on Chiralcel OD using a hexane:isopropanol eluent) are of purified product, 3, which was identified by $^1$H NMR.

The nature of the solvent and temperature have been known to influence enantioselectivity (Lam et al. (1986) *J. Org. Chem.*, 51-2047-2050, Holmberg and Hult (1991) *Biotechnol. Lett.*, 13: 323-326), and the effects of these parameters on the N62C—S—CH$_3$ catalyzed transesterifications was considered next. In this study, CH$_3$CN was selected as the illustrative solvent since the relatively slow rates in tert-BuOH, even at 50° C., precluded the probing of low temperature effects. We included M22C in this part of our study, because it has been found that the M222A mutant of subtilisin BPN' allowed a faster initial reaction of sterically hindered amine nucleophiles with ester acyl donors (Sears et al. (1994) *J. AM. Chem. Soc.*, 116: 6521-6530). The results are shown in Table 5.

TABLE 5

Yields and d.e. values of 3 for reactions carried out in CH₃CN at 4° C.

| Enzyme | 2-phenyl-1-propanol | | 2-methyl-1-pentanol | | 2-phenyl-1-propanol | | 2-octanol | |
|---|---|---|---|---|---|---|---|---|
| | % yield % de | Abs. Conf. | % yield % de | Abs. Conf. | % yield % de | Abs. Conf. | % yield % de | Abs. Conf. |
| WT | 99, 37 (48 hr)³ | R | 91, 4 (24 hr)³ | R | 19, 84 (50 hr) | S | 10, 88 (50 hr) | S |
| M222C | 71, 24 (24 hr) | R | 94, 9 (16 hr) | R | 98, 93 (44 hr) | S | 92, 95 (44 hr) | S |
| N62C—S—CH₃ | 94, 45 (16 hr) | R | 95, 12 (7 hr) | R | 40, 80 (50 hr) | S | 50, 97 (72 hr) | S |

Conditions:
All reactions used 10 equiv. of alcohol,
1, and the acyl donor, 2, in CH3CN at 4° C. as described in Lloyd et al. (1998) *Tetrahedron Asymmetry*, 9: 551-561. All yields and diastereomeric excess (d.e.) (HPLC on Chiralcell OD using a hexane:isopropanol eluent) are of purified product, 3, which was identified by ¹H NMR (Id.).

In $CH_3CN$ at 4° C., M222C and N62-C—S—CH₃ performed better than WT. Both enzymes catalyzed the transesterification of primary and secondary alcohols faster than WT and with de's that were comparable to WT. Remarkably, they gave much higher yield of product ester than WT when the sterically hindered secondary alcohols were used as nucleophiles.

M222C gave almost quantitative yield product ester with 1-phenylethanol and an excellent yield (92%) of ester with 2-octanol. M222C improved the de of product ester to above 90% for both secondary alcohols and N62C—S—CH₃ gave product ester in 97% de for 2-octanol.

From these results, both N62C—S—CH₃ and M222C were seen to be better transesterification catalysts than WT. The reasons for this appear to be different. N62C—S—CH₃ catalyzed the transesterification of primary alcohols with 2 in higher yield and in shorter time than M222C, but the reverse was true for secondary alcohols where M222C efficiently coupled 1-phenylethanol and 2-octanol with 2 in 98% and 92% yields respectively. Without being bound to a particular theory, we have proposed that WT gives lower yields with secondary alcohols because branching at the α-carbon of the alcohol is poorly tolerated by the $S_1'$ pocket (nomenclature according to Schechter and Berger (1967) *Biochem. Biophys. Res. Commun.*, 27: 1570-162) of SBL. Residue 222 of SBL is at the boundary between the $S_1$- and $S_1'$-pockets, a region in close proximity to a location where the nucleophile would approach the acyl-enzyme intermediate in order to deacylate the enzyme and complete the catalytic cycle. Therefore, it is reasonable to expect that if methionine is replaced by the smaller cysteine at position 222, a larger space in this critical region would permit more sterically hindered nucleophiles to react with the acyl-enzyme intermediate. This is exactly what was observed for M222C catalyzed reactions of secondary alcohols. In contrast, residue 62 of SBL is in the $S_2$ pocket, and therefore it is unlikely that any mutation or modification at this residue would significantly influence the $S_1'$ pocket. Nevertheless, N62C—S—CH₃ gave considerably higher yields than WT with secondary alcohols. Further more, this CMM catalyzed the transesterification of primary alcohols much faster than either WT or M222C. It is probable that N62C—S—CH₃ catalyzed transesterification faster than M222C or WT because of a higher turnover rate (Plettner et al. (198) *Bioorg. Med. Chem. Lett.*, 8: 2291-2296), but that in the case of secondary alcohols, the improved catalytic efficiency could not entirely overcome the negative steric hindrance factors.

In conclusion, the future potential of the CMM approach is evident from the fact that both N62C—S—CH₃ and M222C are superior transesterification catalysts to WT, with N62C—S—CH₃ giving higher yields in a shorter reaction time in transesterification reactions that WT when primary alcohols are used with 2 as acyl donor. Furthermore, M222C itself has been found to be an excellent catalyst for the transesterification of secondary alcohols.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A modified subtilisin that catalyzes a transamidation or a transpeptidation or a transesterification reaction and has a replacement by cysteine of one or more amino acid residues at residue positions selected from the group consisting of residue position 156 in the S1 subsite, residue position 166 in the S1 subsite, residue position 217 in the S1' subsite, and residue position 62 in the S2 subsite, wherein the amino acid residue positions are numbered by correspondence with the residue positions in the amino acid sequence of *Bacillus amyloliquifaciens* subtilisin, and wherein the replacement cysteine is modified by replacing the thiol hydrogen in the cysteine with a substituent selected from the group consisting of (R)-2-methoxy-2-phenyl-ethylmethanethiosulfonate,
(S)-2-methoxy-2-phenyl-ethylmethanethiosulfonate,
(R)-2-hydroxy-2-phenyl-ethylmethanethiosulfonate,
(S)-2-hydroxy-2-phenyl-ethylmethanethiosulfonate,
N-(3'-methanethiosulfonatopropyl)-2-oxazoldinone,
N-(3'-methanethiosulfonatopropyl)-(R)-4-isopropyl-2-oxazolidinone,
N-(3'-methanethiosulfonatopropyl)-(S)-4-isopropyl-2-oxazolidinone,
N-(3'-methanethiosulfonatopropyl)-(R)-4-phenyl-2-oxazolidinone,
N-(3'-methanethiosulfonatopropyl)-(S),-4-phenyl-2-oxazolidinone,
N-(3'-methanethiosulfonatopropyl)-(R)-4-benzyl-2-oxazolidinone,
N-(3'-methanethiosulfonatopropyl)-(S)-4-benzyl-2-oxazolidinone, N-(2'-methanethiosulfonatoethyl)-(R)-4-phenyl-2-oxazolidinone,
N-(2'-methanethiosulfonatoethyl)-(S)-4-phenyl-2-oxazolidinone,
N-(2'-methanethiosulfonatopropyl)-(R)-4-benzyl-2-oxazolidinone,
N-(2'-methanethiosulfonatopropyl)-(S)-4-benzyl-2-oxazolidinone,
N-(3'-methanethiosulfonatopropyl)-(3aR-cis)-3,3a-8,8a-tetrahydro-2H-indeno[1,2-d]-oxazol-2-one, and
N-(3'-methanethiosulfonatopropyl)-(3aS-cis)-3,3a-8,8a-tetrahydro-2H-indeno[1,2-d]-oxazol-2-one.

2. The modified subtilisin of claim 1, wherein said reaction catalyzed by said modified subtilisin is stereoselective.

3. The modified subtilisin of claim 1, wherein the amino acid replaced with a cysteine is selected from the group consisting of asparagine, leucine, methionine, and serine.

4. A chemically modified mutant subtilisin having a replacement by cysteine of one or more amino acid residues at residue positions selected from the group consisting of residue position 62, residue position 156, residue position 166, and residue position 217, wherein the amino acid residue positions are numbered by correspondence with the residue positions in the amino acid sequence of *Bacillus amyloliquifaciens* subtilisin, and wherein the replacement cysteine is modified by replacing the thiol hydrogen in the cysteine with a substituent selected from the group consisting of
(R)-2-methoxy-2-phenyl-ethylmethanethiosulfonate,
(S)-2-methoxy-2-phenyl-ethylmethanethiosulfonate,
(R)-2-hydroxy-2-phenyl-ethylmethanethiosulfonate,
(S)-2-hydroxy-2-phenyl-ethylmethanethiosulfonate,
N-(3'-methanethiosulfonatopropyl)-2-oxazolidinone,
N-(3'-methanethiosulfonatopropyl)-(R)-4-isopropyl-2-oxazolidinone,
N-(3'-methanethiosulfonatopropyl)-(S)-4-isopropyl-2-oxazolidinone,
N-(3'-methanethiosulfonatopropyl)-(R)-4-phenyl-2-oxazolidinone,
N-(3'-methanethiosulfonatopropyl)-(S),-4-phenyl-2-oxazolidinone,
N-(3'-methanethiosulfonatopropyl)-(R)-4-benzyl-2-oxazolidinone,
N-(3'-methanethiosulfonatopropyl)-(S)-4-benzyl-2-oxazolidinone,
N-(2'-methanethiosulfonatoethyl)-(R)-4-phenyl-2-oxazolidinone,
N-(2'-methanethiosulfonatoethyl)-(S)-4-phenyl-2-oxazolidinone,
N-(2'-methanethiosulfonatopropyl)-(R)-4-benzyl-2-oxazolidinone,
N-(2'-methanethiosulfonatopropyl)-(S)-4-benzyl-2-oxazolidinone,
N-(3'-methanethiosulfonatopropyl)-(3aR-cis)-3,3a-8,8a-tetrahydro-2H-indeno[1,2-d]-oxazol-2-one, and
N-(3'-methanethiosulfonatopropyl)-(3aS-cis)-3,3a-8,8a-tetrahydro-2H-indeno[1,2-d]-oxazol-2-one.

* * * * *

UNITED STATES PATENT AND TRADEMARK OFFICE
CERTIFICATE OF CORRECTION

PATENT NO.         : 8,148,128 B2
APPLICATION NO.    : 12/234399
DATED              : April 3, 2012
INVENTOR(S)        : John Bryan Jones, Michael Dickman and Richard C. Lloyd It is certified that error appears in the above-identified patent and that said Letters Patent is hereby corrected as shown below:

Claim 1, column 37, lines 9 and 11, delete "-3,3a-8,8a-" and replace with -- ⁻3,3a,8,8a- --.

Claim 4, column 38, lines 24 and 26, delete "-3,3a-8,8a-" and replace with -- ⁻3,3a,8,8a- --.

Signed and Sealed this
Twenty-ninth Day of May, 2012

David J. Kappos
*Director of the United States Patent and Trademark Office*